(12) United States Patent
Bastiaans et al.

(10) Patent No.: US 7,767,664 B2
(45) Date of Patent: Aug. 3, 2010

(54) PLANT GROWTH REGULATION

(75) Inventors: Henricus M. M. Bastiaans, Usingen (DE); Günter Donn, Hofheim (DE); Nathalie Knittel, Kriftel (DE); Arianna Martelletti, Sulzbach (DE); Richard Rees, Alexander Drive, NC (US); Michael Schwall, Baden-Baden (DE); Ryan Whitford, Gent (BE)

(73) Assignee: Bayer CropScience AG, Monheim (DE)

( * ) Notice: Subject to any disclaimer, the term of this patent is extended or adjusted under 35 U.S.C. 154(b) by 399 days.

(21) Appl. No.: 11/596,230

(22) PCT Filed: Apr. 30, 2005

(86) PCT No.: PCT/EP2005/004687

§ 371 (c)(1),
(2), (4) Date: Apr. 30, 2008

(87) PCT Pub. No.: WO2005/107471

PCT Pub. Date: Nov. 17, 2005

(65) Prior Publication Data

US 2008/0269055 A1 Oct. 30, 2008

(30) Foreign Application Priority Data

May 12, 2004 (EP) .................... 04011256

(51) Int. Cl.
*A01N 43/00* (2006.01)
*A01N 43/40* (2006.01)
*A01N 43/36* (2006.01)
*A01N 43/46* (2006.01)
*A61K 31/55* (2006.01)

(52) U.S. Cl. .................. 514/212.03; 504/129; 504/130; 504/179; 504/218; 514/212.01; 514/212.04

(58) Field of Classification Search .................. None
See application file for complete search history.

(56) References Cited

U.S. PATENT DOCUMENTS

| 6,610,684 | B2 * | 8/2003 | Zaharevitz et al. ..... 514/212.06 |
| 2003/0181439 | A1 * | 9/2003 | Meijer et al. ........... 514/212.06 |
| 2004/0224938 | A1 | 11/2004 | Sattlegger et al. |

FOREIGN PATENT DOCUMENTS

| WO | WO 99/65910 A1 | 12/1999 |
| WO | WO 01/60374 A1 | 8/2001 |
| WO | WO 03/037873 A1 | 5/2003 |

OTHER PUBLICATIONS

Angewante Chemie 2003, 42, 2122-2138.*
J. Med. Chem. 1999, 42, 2909-2919.*
Antimicrobial agents and chemotherapy 2004, 48, 3033-3042.*
International Search Report of International Application No. PCT/EP2005/004687, European Patent Office, Netherlands, mailed on Jun. 13, 2005.

* cited by examiner

*Primary Examiner*—Ernst V Arnold
*Assistant Examiner*—Jessica Kassa
(74) *Attorney, Agent, or Firm*—Sterne, Kessler, Goldstein & Fox, P.L.L.C.

(57) ABSTRACT

The present invention relates to a new class of plant growth regulators. In particular, the invention relates to fused azepinone derivative of general formula (I) or an agriculturally acceptable salt thereof wherein X is $CO_2R^2$ or H; Y is OH; $NHNR^3R^4$, $NHNHC(=Z)NR^5R^6$ or $NHNHC(=Z)CR^7R^8R^9$; or X and Y together with the two carbon atoms to which they are attached form a ring of formula (A) and a method for treatment of plants with such compounds in order to induce growth regulating responses.

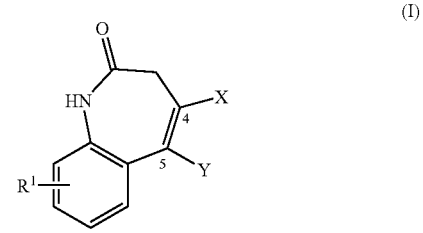

(I)

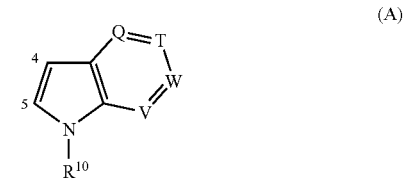

(A)

12 Claims, No Drawings

PLANT GROWTH REGULATION

This application is a National Stage of International Application No. PCT/EP2005/004687, filed Apr. 30, 2005, which claims the benefit of European Patent Application No. 04011256.7, filed May 12, 2004. The entirety of these applications is incorporated by reference herein.

Present invention relates to the technical field of agrochemicals and methods used in agriculture for plant growth regulation. In particular, the present invention relates to a new class of plant growth regulators for the treatment of plants in order to induce growth regulating responses which result in superior growth of treated plants, certain parts of the plants or, more generally, crop yield.

The term "method for plant growth regulation" or the term "growth regulation process" or the use of the words "plant growth regulation" or other terms using the word "regulate" relate to a variety of plant responses which improve some characteristic of the plant. "Plant growth regulators" are compounds which possess activity in one or more growth regulation process(es) of a plant.

Plant growth regulation is distinguished here from pesticidal action or growth reduction, sometimes also defined as a plant growth regulation, the intention of which, however, is to destroy or stunt the growth of a plant. For this reason, the compounds used in the practice of this invention are used in amounts which are non-phytotoxic with respect to the plant being treated but which stimulate the growth of the plant or certain parts thereof. Therefore, such compounds may also be called "plant stimulants", their action may be called as "plant growth stimulation".

Plant growth regulation is a desirable way to improve plants and their cropping so as to obtain improved plant growth and better conditions of agriculture practice compared to non-treated plants. This kind of molecules can either inhibit or promote cellular activities. This means that plant growth regulators identified in plants most often regulate division, elongation and differentiation of plant cells in a way that, most often, they have multiple effects in plants. The trigger event can be seen to be different in plants in comparison to the one known from animals.

On the molecular basis, plant growth regulators may work by affecting membrane properties, controlling gene expression or affecting enzyme activity or being active in a combination of at least two of the before mentioned types of interaction. Plant growth regulators are chemicals either of natural origin, also called plant hormones (like non-peptide hormones e.g. auxins, giberrellins, cytokinins, ethylene, brassinosteroids or abscisic acid, and salicylic acid), lipooligosaccharides (e.g. Nod factors), peptides (e.g. systemin), fatty acid derivatives (e.g. jasmonates), and oligosaccharins (for review see: Biochemistry & Molecular Biology of the Plant (2000); eds. Buchanan, Gruissem, Jones, pp. 558-562; and 850-929), or they can be synthetically produced compounds (like derivatives of naturally occurring plant growth hormones, ethephon).

Plant growth regulators which work at very small concentrations can be found in many cells and tissues, but they seem to be concentrated in meristems and buds. Beside the selection of the right compound it is also relevant to look for the optimal environmental conditions because there are several factors known that may affect the action of growth hormones, like (a) the concentration of the plant growth regulator itself, (b) the quantity applied to the plant, (c) the time of application in relation to flowering date, (d) temperature and humidity prior to and after treatment, (e) plant moisture content, and several others.

The mode of action of existing plant growth regulators often is not known. Various targets are discussed and among those, most of the affected molecules are involved in cell division regulation, like arresting the cell cycle in stage G1 or G2, respectively, others for signaling drought stress responses (Biochemistry & Molecular Biology of the Plant (2000); eds. Buchanan, Gruissem, Jones, pp. 558-560). In any case, the hormone control can be identified as an extremely complex cascade of up and down regulations which, for example, can lead to a growth stimulation of one organ or cell typus of a plant but also can lead to a repression in other organs or cell typus of the same plant.

In many cases, kinases are involved either directly or indirectly in plant hormone control and among the kinases, protein kinases are central and highly specific control molecules in respect to cell cycle control. Such kinases are discussed as targets for several plant hormones, like it is the case for auxin and abscisic acid (Biochemistry & Molecular Biology of the Plant (2000); eds. Buchanan, Gruissem, Jones, pp. 542-565 and pp. 980-985; Morgan (1997), Annu. Rev. Cell. Dev. Biol., 13, 261-291; Amon et al. (1993), Cell, 74, pp. 993-1007; Dynlacht et al. (1997), Nature, 389, pp. 149-152; Hunt and Nasmyth (1997), Curr. Opin. Cell. Biol., 9, pp. 765-767; Thomas and Hall (1997), Curr. Opin. Cell Biol., 9, pp. 782-787).

WO 99/65910 teaches that certain fused azepinone derivatives act as inhibitors of cyclin dependent kinases (CDKs) and may be effective in pharmaceutical use, especially in treatment of tumours or other cell proliferation disorders of mammals but it does not teach or even suggest that plant growth can be stimulated by this class of compounds.

The present invention relates to the use of a compound for plant growth regulation, preferably by application of the compound to plants, to the seeds from which they grow or to the locus in which they grow, in an effective plant growth regulating, preferably non-phytotoxic amount, which compound is a fused azepinone derivative of formula (I) or an agriculturally acceptable salt thereof:

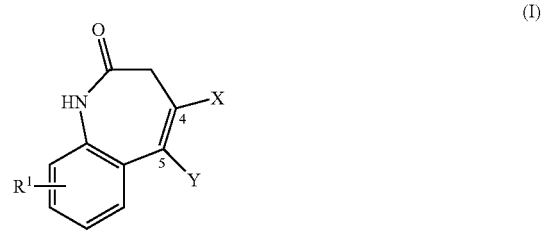

wherein:

X is $CO_2R^2$ or H;

Y is OH; $NHNR^3R^4$, $NHNHC(=Z)NR^5R^6$ or $NHNHC(=Z)CR^7R^8R^9$; or

X and Y together with the two carbon atoms to which they are attached form a ring of formula (A):

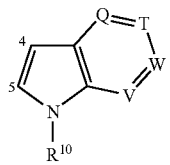
(A)

wherein the carbon atoms marked 4 and 5 respectively correspond to the carbon atoms marked 4 and 5 in formula (I);

Q, T, W and V are each independently $CR^{11}$ or a N atom, providing that a maximum of one of Q, T, W and V is a N atom;

Z is O or S;

$R^1$ and $R^{11}$ are each independently H, halogen, hydroxy, amino, nitro, formyl, carboxy, cyano, thiocyanato, aminocarbonyl, $(C_1\text{-}C_6)$alkoxy, $(C_1\text{-}C_6)$haloalkoxy, $(C_1\text{-}C_6)$alkyl-$S(O)_n$, $(C_1\text{-}C_6)$haloalkyl-$S(O)_n$, $(C_1\text{-}C_6)$alkylamino, di[$(C_1\text{-}C_6)$alkyl]amino, $(C_1\text{-}C_6)$alkylcarbonyl, $(C_1\text{-}C_6)$alkoxycarbonyl, $(C_1\text{-}C_6)$alkylaminocarbonyl, di[$(C_1\text{-}C_6)$alkyl]aminocarbonyl, N—$(C_1\text{-}C_6)$alkanoylamino, N—$(C_1\text{-}C_6)$alkanoyl-N—$(C_1\text{-}C_6)$alkylamino, sulfamoyl, N—$(C_1\text{-}C_6)$alkylsulfamoyl, N,N-di[$(C_1\text{-}C_6)$alkyl]sulfamoyl, $(C_3\text{-}C_9)$cycloalkyl, $(C_1\text{-}C_6)$alkyl, $(C_2\text{-}C_6)$alkenyl and $(C_2\text{-}C_6)$alkynyl, where each of the last-mentioned 3 radicals is unsubstituted or substituted by one or more radicals selected from the group consisting of halogen, hydroxy, amino, nitro, carboxy, cyano, $(C_1\text{-}C_4)$alkoxy, $(C_1\text{-}C_4)$haloalkoxy, $(C_1\text{-}C_4)$alkyl-$S(O)_n$, $(C_1\text{-}C_4)$haloalkyl-$S(O)_n$, $(C_1\text{-}C_4)$alkylamino, di[$(C_1\text{-}C_4)$alkyl]amino, $(C_3\text{-}C_9)$cycloalkyl, $(C_1\text{-}C_4)$alkylcarbonyl, $(C_1\text{-}C_4)$alkoxycarbonyl, phenyl, phenoxy, phenylthio, heterocyclyl, heteroaryloxy and heteroarylthio, where each of the last-mentioned 6 radicals is unsubstituted or has one or more substituents selected from the group consisting of halogen, nitro, formyl, cyano, $(C_1\text{-}C_4)$alkyl, $(C_1\text{-}C_4)$alkoxy, $(C_1\text{-}C_4)$alkyl-$S(O)_n$, $(C_1\text{-}C_4)$haloalkyl-$S(O)_n$, $(C_1\text{-}C_4)$haloalkyl, $(C_1\text{-}C_4)$haloalkoxy, $(C_1\text{-}C_4)$alkylcarbonyl and $(C_1\text{-}C_4)$alkoxycarbonyl;

or phenyl, phenoxy, phenylthio, phenylcarbonyl, heteroaryl, heteroaryloxy and heteroarylthio, where each of the last-mentioned 7 radicals is unsubstituted or substituted by one or more radicals selected from the group consisting of halogen, hydroxy, amino, nitro, carboxy, formyl, cyano, $(C_1\text{-}C_4)$alkyl, $(C_1\text{-}C_4)$haloalkyl, $(C_1\text{-}C_4)$alkoxy, $(C_1\text{-}C_4)$haloalkoxy, $(C_1\text{-}C_4)$alkyl-$S(O)_n$, $(C_1\text{-}C_4)$haloalkyl-$S(O)_n$, $(C_1\text{-}C_4)$alkylamino, di[$(C_1\text{-}C_4)$alkyl]amino, $(C_1\text{-}C_4)$alkylcarbonyl, $(C_1\text{-}C_4)$alkoxycarbonyl and in the case of heteroaryl also oxo, where heteroaryl in the above-mentioned radicals independently of one another in each case is a mono-, bi- or tricyclic heteroaromatic ring system in which at least 1 ring contains one or more hetero atoms (preferably 1, 2 or 3 hetero atoms) selected from the group consisting of N, O and S, and which contains a total of 5 to 14 (preferably 5 to 7) ring atoms wherein at least one ring is fully unsaturated (any further rings being unsaturated, or partially or fully hydrogenated); and heterocyclyl is a heterocyclic radical having 3 to 7 ring atoms and 1 to 3 hetero atoms selected from the group consisting of N, O and S;

$R^2$ is $(C_1\text{-}C_6)$alkyl, $(C_3\text{-}C_9)$cycloalkyl, $(C_1\text{-}C_6)$alkyl, $(C_2\text{-}C_6)$alkenyl, $(C_2\text{-}C_6)$alkynyl, $(C_1\text{-}C_4)$alkoxy-$(C_1\text{-}C_4)$alkyl;

$R^3$ is $(C_1\text{-}C_6)$alkyl, $(C_2\text{-}C_6)$alkenyl, $(C_2\text{-}C_6)$alkynyl, phenyl-$(CH_2)_m$ or heteroaryl, where heteroaryl is a mono-, bi- or tricyclic heteroaromatic ring system in which at least 1 ring contains one or more hetero atoms (preferably 1, 2 or 3 hetero atoms) selected from the group consisting of N, O and S, and which contains a total of 5 to 14 (preferably 5 to 7) ring atoms wherein at least one ring is fully unsaturated (any further rings being unsaturated, or partially or fully hydrogenated) which is unsubstituted or substituted by one or more radicals selected from the group consisting of halogen, hydroxy, amino, nitro, carboxy, formyl, cyano, $(C_1\text{-}C_4)$alkyl, $(C_1\text{-}C_4)$haloalkyl, $(C_1\text{-}C_4)$alkoxy, $(C_1\text{-}C_4)$haloalkoxy, $(C_1\text{-}C_4)$alkyl-$S(O)_n$, $(C_1\text{-}C_4)$haloalkyl-$S(O)_n$, $(C_1\text{-}C_4)$alkylamino, di[$(C_1\text{-}C_4)$alkyl]amino, $(C_1\text{-}C_4)$alkylcarbonyl, $(C_1\text{-}C_4)$alkoxycarbonyl and oxo;

$R^4$, $R^6$, $R^8$, $R^9$ and $R^{10}$ are each independently H or $(C_1\text{-}C_6)$alkyl;

$R^5$ is H or $R^3$;

$R^7$ is as defined for $R^3$ wherein m is zero;

m is 0 or 1; and n is 0, 1 or 2.

These compounds possess valuable plant growth regulatory properties.

The invention also encompasses any stereoisomer, enantiomer, geometric isomer or tautomer, and mixtures of the compounds of formula (I). Examples of typical tautomer forms are shown hereinafter in formulae (Ie) and (If).

By the term "agriculturally acceptable salts" is meant salts the anions or cations of which are known and accepted in the art for the formation of salts for agricultural use.

Suitable salts with bases, e.g. formed by compounds of formula (I) containing a carboxylic acid group, include alkali metal (e.g. sodium and potassium), alkaline earth metal (e.g. calcium and magnesium) and ammonium salts. The ammonium salts include ammonium ($NH_4^+$) and ammonium salts of organic amines, (e.g. the diethanolamine, triethanolamine, octylamine, morpholine and dioctylmethylamine salts) and quaternary ammonium salts ($NR_4^+$). Suitable acid addition salts, e.g. formed by compounds of formula (I) containing an amino group, include salts with inorganic acids, for example hydrochlorides, sulphates, phosphates and nitrates and salts with organic acids for example acetic acid.

In the present patent specification, including the accompanying claims, the aforementioned substituents have the following meanings:

A "heteroaryl" group is a mono-, bi- or polycyclic heteroaromatic ring system in which at least 1 ring contains one or more hetero atoms (preferably 1, 2 or 3 hetero atoms) selected from the group consisting of N, O and S, and which contains a total of 5 to 14 (preferably 5 to 7) ring atoms wherein at least one ring is fully unsaturated (any further rings being unsaturated, or partially or fully hydrogenated). The heteroaryl group is for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl, triazolyl, benzothienyl, benzofuranyl, indolyl, isothiazolyl, benzotriazolyl, benzisoxazolyl, isoindolyl, benzoxazolyl, benzimidazolyl, quinolyl, tetrahydroquinolyl, isoquinolyl, dihydroindolyl, benzo[1,4]dioxanyl or 6,7,8,9-tetrahydropyrido[1,2-a]indolyl. The "heteroaryl" group may be unsubstituted or substituted, preferably by one or more radicals (preferably 1, 2 or 3 radicals) selected from the group consisting of halogen, alkoxy, haloalkoxy, alkylthio, haloalkylthio, hydroxy, amino, nitro, carboxy, cyano, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl, alkyl, haloalkyl and oxo.

The oxo group can also be present at those hetero ring atoms where various oxidation numbers are possible, for example in the case of N and S.

In formula (I) and all subsequent formulae, the radicals alkyl, alkoxy, haloalkyl, haloalkoxy, alkylamino and alkylthio and the corresponding unsaturated and/or substituted radicals can be in each case straight-chain or branched in the carbon skeleton. Unless specifically indicated, the lower carbon skeletons, for example those having 1 to 6 carbon atoms or, in the case of unsaturated groups, 2 to 6 carbon atoms, are preferred for these radicals.

Halogen means fluorine, chlorine, bromine or iodine.

The term "halo" before the name of a radical means that this radical is partially or completely halogenated, that is to say, substituted by F, Cl, Br, or I, in any combination.

The expression "$(C_1-C_6)$alkyl" means an unbranched or branched non-cyclic saturated hydrocarbon radical having 1, 2, 3, 4, 5 or 6 carbon atoms (indicated by a range of C-atoms in the parenthesis), such as, for example a methyl, ethyl, propyl, isopropyl, 1-butyl, 2-butyl, 2-methylpropyl or tert-butyl radical. The same applies to alkyl groups in composite radicals such as "alkoxyalkyl".

Alkyl radicals and also in composite groups, unless otherwise defined, preferably have 1 to 4 carbon atoms.

"$(C_1-C_6)$Haloalkyl" means an alkyl group mentioned under the expression "$(C_1-C_6)$alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2CH_2Cl$.

"$(C_1-C_4)$Alkoxy-$(C_1-C_6)$alkyl" means $(C_1-C_6)$alkyl which is substituted by $(C_1-C_4)$alkoxy.

"$(C_1-C_6)$Alkyl-$S(O)_n$" means $(C_1-C_6)$alkylthio, alkylsulfinyl or alkylsulfonyl group, for example methylthio, methylsulfinyl or methylsulfonyl.

"$(C_1-C_6)$Alkoxy" means an alkoxy group whose carbon chain has the meaning given under the expression "$(C_1-C_6)$alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_1-C_6)$Alkylcarbonyl" means a $(C_1-C_6)$alkyl group which is attached to a carbonyl group.

"$(C_1-C_6)$Alkoxycarbonyl" means a $(C_1-C_6)$alkoxy group which is attached to a carbonyl group.

"$(C_2-C_6)$Alkenyl" means an unbranched or branched non-cyclic carbon chain having a number of carbon atoms which corresponds to this stated range and which contains at least one double bond which can be located in any position of the respective unsaturated radical. "$(C_2-C_6)$Alkenyl" accordingly denotes, for example, the vinyl, allyl, 2-methyl-2-propenyl, 2-butenyl, pentenyl, 2-methylpentenyl or the hexenyl group.

"$(C_2-C_6)$Alkynyl" means an unbranched or branched non-cyclic carbon chain having a number of carbon atoms which corresponds to this stated range and which contains one triple bond which can be located in any position of the respective unsaturated radical. "$(C_2-C_6)$Alkynyl" accordingly denotes, for example, the propargyl, 1-methyl-2-propynyl, 2-butynyl or 3-butynyl group.

"$(C_3-C_6)$Cycloalkyl" denotes monocyclic alkyl radicals, such as the cyclopropyl, cyclobutyl, cyclopentyl or cyclohexyl radical.

A heterocyclyl radical can be saturated, unsaturated or heteroaromatic; it preferably contains one or more, in particular 1, 2 or 3, hetero atoms in the heterocyclic ring, preferably selected from the group consisting of N, O and S; it is preferably an aliphatic heterocyclyl radical having 3 to 7 ring atoms or a heteroaromatic radical having 5 or 6 ring atoms. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, or it is a partially or fully hydrogenated radical such as oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl. Suitable substituents for a substituted heterocyclic radical are the substituents stated further below, and additionally also oxo. The oxo group can also be present at those hetero ring atoms where various oxidation numbers are possible, for example in the case of N and S.

Substituted radicals such as a substituted alkyl, alkenyl, alkynyl, aryl, phenyl, benzyl, heterocyclyl and heteroaryl radical are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl.

In this context, "one or more radicals selected from the group consisting of" in the definition are to be understood as meaning in each case one or more identical or different radicals selected from the stated group of radicals, unless specific limitations are defined expressly.

The term "substituted radicals" such as substituted alkyl and the like includes, in addition to the saturated hydrocarbon-containing radicals stated, corresponding unsaturated aliphatic and aromatic radicals such as unsubstituted or substituted alkenyl, alkynyl, alkenyloxy, alkynyloxy, phenyl, phenoxy and the like, as substituents. In the case of substituted cyclic radicals with aliphatic moieties in the ring, this also encompasses cyclic systems with those substituents which are bonded to the ring by a double bond, for example which are substituted by an alkylidene group such as methylidene or ethylidene.

In the case of radicals with carbon atoms, those having 1 to 4 carbon atoms, in particular 1 or 2 carbon atoms, are preferred. Substituents which are preferred are, as a rule, those selected from the group consisting of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Especially preferred in this context are the substituents methyl, methoxy and chlorine.

Preferably Y is OH; or

X and Y together with the two carbon atoms to which they are attached form a ring of formula (A) as defined above.

Preferably X is $CO_2R^2$ or H; and Y is OH; or

X and Y together with the two carbon atoms to which they are attached form a ring of formula (A) above, wherein Q, T, W and V are each $CR^{11}$, $R^{11}$ is as defined above and $R^{10}$ is H.

Preferably $R^1$ and $R^{11}$ are each independently H, halogen, hydroxy, amino, nitro, formyl, carboxy, cyano, thiocyanato, aminocarbonyl, $(C_1-C_4)$alkoxy, $(C_1-C_4)$haloalkoxy, $(C_1-C_4)$alkyl-$S(O)_n$, $(C_1-C_4)$haloalkyl-$S(O)_n$, $(C_1-C_4)$alkylamino, di[$(C_1-C_4)$]alkylamino, $(C_1-C_4)$alkylcarbonyl, $(C_1-C_4)$ alkoxycarbonyl, $(C_1-C_4)$alkylaminocarbonyl, di[$(C_1-C_4)$alkyl]aminocarbonyl, N—$(C_1-C_4)$alkanoylamino, N—$(C_1-C_4)$alkanoyl-N—$(C_1-C_4)$alkylamino, sulfamoyl, N—$(C_1-C_4)$alkylsulfamoyl, N,N-di[$(C_1-C_4)$alkyl]sulfamoyl, $(C_3-C_6)$cycloalkyl, $(C_1-C_4)$alkyl, $(C_2-C_4)$alkenyl and $(C_2-C_4)$alkynyl, where each of the last-mentioned 3 radicals is unsubstituted or substituted by one or more radicals selected from the group consisting of halogen, hydroxy, amino, nitro, carboxy, cyano, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_3-C_6)$cycloalkyl, $(C_1-C_4)$alkylcarbonyl, $(C_1-C_4)$alkoxycarbonyl or phenyl, phenoxy, phenylthio, heterocyclyl, heteroaryloxy and heteroarylthio, where each of the last-mentioned 6 radicals is unsubstituted or has one or more substituents selected from the group consisting of halogen, nitro, cyano, $(C_1-C_4)$alkyl, $(C_1-C_4)$alkoxy, $(C_1-C_4)$alkyl-S(O)$_n$, $(C_1-C_4)$haloalkyl-S(O)$_n$, $(C_1-C_4)$haloalkyl, $(C_1-C_4)$haloalkoxy, $(C_1-C_4)$alkylcarbonyl and $(C_1-C_4)$alkoxycarbonyl;

or phenyl, phenoxy, phenylthio, phenylcarbonyl, heteroaryl, heteroaryloxy and heteroarylthio, where each of the last-mentioned 7 radicals is unsubstituted or substituted by one or more radicals selected from the group consisting of halogen, hydroxy, amino, nitro, carboxy, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_1-C_4)$alkylcarbonyl, $(C_1-C_4)$alkoxycarbonyl and in the case of heteroaryl also oxo, where heteroaryl in the abovementioned radicals independently of one another in each case is a mono-, bi- or tricyclic heteroaromatic ring system in which at least 1 ring contains one or more hetero atoms (preferably 1, 2 or 3 hetero atoms) selected from the group consisting of N, O and S, and which contains a total of 5 to 14 (preferably 5 to 7) ring atoms wherein at least one ring is fully unsaturated (any further rings being unsaturated, or partially or fully hydrogenated); and heterocyclyl is a heterocyclic radical having 3 to 7 ring atoms and 1 to 3 hetero atoms selected from the group consisting of N, O and S.

More preferably $R^1$ and $R^{11}$ are each independently H, halogen, hydroxy, amino, nitro, formyl, carboxy, cyano, thiocyanato, aminocarbonyl, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_1-C_4)$alkylcarbonyl, $(C_1-C_4)$alkoxycarbonyl, $(C_1-C_4)$alkylaminocarbonyl, di[$(C_1-C_4)$alkyl]aminocarbonyl, N—$(C_1-C_4)$alkanoylamino, N—$(C_1-C_4)$alkanoyl-N—$(C_1-C_4)$alkylamino, sulfamoyl, N—$(C_1-C_4)$alkylsulfamoyl, N,N-di[$(C_1-C_4)$alkyl]sulfamoyl, $(C_3-C_6)$cycloalkyl, $(C_1-C_4)$alkyl, $(C_2-C_4)$alkenyl and $(C_2-C_4)$alkynyl, where each of the last-mentioned 3 radicals is unsubstituted or substituted by one or more radicals selected from the group consisting of halogen, hydroxy, amino, cyano, $(C_1-C_4)$alkoxy, $(C_1-C_4)$haloalkoxy, $(C_1-C_4)$alkylamino, di[$(C_1-C_4)$alkyl]amino, $(C_3-C_6)$cycloalkyl, $(C_1-C_4)$alkoxycarbonyl and phenyl, where the last-mentioned radical is unsubstituted or has one or more substituents selected from the group consisting of halogen, nitro, cyano, $(C_1-C_4)$alkyl, $(C_1-C_4)$alkoxy, $(C_1-C_4)$alkyl-S(O)$_n$, $(C_1-C_4)$haloalkyl-S(O)$_n$, $(C_1-C_4)$haloalkyl, $(C_1-C_4)$haloalkoxy, $(C_1-C_4)$alkylcarbonyl and $(C_1-C_4)$alkoxycarbonyl;

or phenyl, phenoxy and heteroaryl, where each of the last-mentioned 3 radicals is unsubstituted or substituted by one or more radicals selected from the group consisting of halogen, hydroxy, amino, nitro, carboxy, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_1-C_4)$alkylcarbonyl, $(C_1-C_4)$alkoxycarbonyl and in the case of heteroaryl also oxo, where heteroaryl in the abovementioned radicals independently of one another in each case is a mono-, bi- or tricyclic heteroaromatic ring system in which at least 1 ring contains one or more hetero atoms (preferably 1, 2 or 3 hetero atoms) selected from the group consisting of N, O and S, and which contains a total of 5 to 14 (preferably 5 to 7) ring atoms wherein at least one ring is fully unsaturated (any further rings being unsaturated, or partially or fully hydrogenated); and heterocyclyl is a heterocyclic radical having 3 to 7 ring atoms and 1 to 3 hetero atoms selected from the group consisting of N, O and S.

Most preferably $R^1$ and $R^{11}$ are each independently H, halogen, OH, $NO_2$, CN, $CO_2H$, $(C_1-C_4)$alkyl, $(C_1-C_4)$haloalkyl, $(C_1-C_4)$alkoxy-$(C_1-C_4)$alkyl, $(C_1-C_4)$alkoxy, $(C_1-C_4)$alkylcarbonyl and $(C_1-C_4)$alkoxycarbonyl.

Preferably $R^{10}$ is H.

A preferred class of compounds of formula (I) for use in the invention are those in which:

X is $CO_2R^2$ or H; and Y is OH; or

X and Y together with the two carbon atoms to which they are attached form a ring of formula (A) above, wherein Q, T, W and V are each $CR^{11}$;

$R^1$ and $R^{11}$ are each independently H, halogen, hydroxy, amino, nitro, formyl, carboxy, cyano, thiocyanato, aminocarbonyl, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_1-C_4)$alkylcarbonyl, $(C_1-C_4)$alkoxycarbonyl, $(C_1-C_4)$alkylaminocarbonyl, di[$(C_1-C_4)$alkyl]aminocarbonyl, N—$(C_1-C_4)$alkanoylamino, N—$(C_1-C_4)$alkanoyl-N—$(C_1-C_4)$alkylamino, sulfamoyl, N—$(C_1-C_4)$alkylsulfamoyl, N,N-di[$(C_1-C_4)$alkyl]sulfamoyl, $(C_3-C_6)$cycloalkyl or $(C_1-C_4)$alkyl, $(C_2-C_4)$alkenyl and $(C_2-C_4)$alkynyl, where each of the last-mentioned 3 radicals is unsubstituted or substituted by one or more radicals selected from the group consisting of halogen, hydroxy, amino, nitro, carboxy, cyano, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_3-C_6)$cycloalkyl, $(C_1-C_4)$alkylcarbonyl, $(C_1-C_4)$alkoxycarbonyl or phenyl, phenoxy, phenylthio, heterocyclyl, heteroaryloxy and heteroarylthio, where each of the last-mentioned 6 radicals is unsubstituted or has one or more substituents selected from the group consisting of halogen, nitro, cyano, $(C_1-C_4)$alkyl, $(C_1-C_4)$alkoxy, $(C_1-C_4)$alkyl-S(O)$_n$, $(C_1-C_4)$haloalkyl-S(O)$_n$, $(C_1-C_4)$haloalkyl, $(C_1-C_4)$haloalkoxy, $(C_1-C_4)$alkylcarbonyl and $(C_1-C_4)$alkoxycarbonyl;

or phenyl, phenoxy, phenylthio, phenylcarbonyl, heteroaryl, heteroaryloxy and heteroarylthio, where each of the last-mentioned 7 radicals is unsubstituted or substituted by one or more radicals selected from the group consisting of halogen, hydroxy, amino, nitro, carboxy, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_1-C_4)$alkylcarbonyl, $(C_1-C_4)$alkoxycarbonyl and in the case of heteroaryl also oxo, where heteroaryl in the abovementioned radicals independently of one another in each case is a mono-, bi- or tricyclic heteroaromatic ring system in which at least 1 ring contains one or more hetero atoms (preferably 1, 2 or 3 hetero atoms) selected from the group consisting of N, O and S, and which contains a total of 5 to 14 (preferably 5 to 7) ring atoms wherein at least one ring is fully unsaturated (any further rings being unsaturated, or partially or fully hydrogenated); and heterocyclyl is a heterocyclic radical having 3 to 7 ring atoms and 1 to 3 hetero atoms selected from the group consisting of N, O and S; and $R^{10}$ is H.

A further preferred class of compounds of formula (I) for use in the invention are those in which:

X is $CO_2R^2$ or H; and Y is OH; or

X and Y together with the two carbon atoms to which they are attached form a ring of formula (A) above, wherein Q, T, W and V are each $CR^{11}$;

$R^1$ and $R^{11}$ are each independently H, halogen, hydroxy, amino, nitro, formyl, carboxy, cyano, thiocyanato, aminocarbonyl, $(C_1-C_4)$alkoxy, $(C_1-C_4)$haloalkoxy, $(C_1-C_4)$alkyl-$S(O)_n$, $(C_1-C_4)$haloalkyl-$S(O)_n$, $(C_1-C_4)$alkylamino, di$[(C_1-C_4)$alkyl]amino, $(C_1-C_4)$alkylcarbonyl, $(C_1-C_4)$alkoxycarbonyl, $(C_1-C_4)$alkylaminocarbonyl, di$[(C_1-C_4)$alkyl]aminocarbonyl, N—$(C_1-C_4)$alkanoylamino, N—$(C_1-C_4)$alkanoyl-N—$(C_1-C_4)$alkylamino, sulfamoyl, N—$(C_1-C_4)$alkylsulfamoyl, N,N-di$[(C_1-C_4)$alkyl]sulfamoyl, $(C_3-C_6)$cycloalkyl or $(C_1-C_4)$alkyl, $(C_2-C_4)$alkenyl and $(C_2-C_4)$alkynyl, where each of the last-mentioned 3 radicals is unsubstituted or substituted by one or more radicals selected from the group consisting of halogen, hydroxy, amino, cyano, $(C_1-C_4)$alkoxy, $(C_1-C_4)$haloalkoxy, $(C_1-C_4)$alkylamino, di$(C_1-C_4)$alkylamino, $(C_3-C_6)$cycloalkyl, $(C_1-C_4)$alkoxycarbonyl and phenyl, where the last-mentioned radical is unsubstituted or has one or more substituents selected from the group consisting of halogen, nitro, cyano, $(C_1-C_4)$alkyl, $(C_1-C_4)$alkoxy, $(C_1-C_4)$alkyl-$S(O)_n$, $(C_1-C_4)$haloalkyl-$S(O)_n$, $(C_1-C_4)$haloalkyl, $(C_1-C_4)$haloalkoxy, $(C_1-C_4)$alkylcarbonyl and $(C_1-C_4)$alkoxycarbonyl;

or phenyl, phenoxy and heteroaryl, where each of the last-mentioned 3 radicals is unsubstituted or substituted by one or more radicals selected from the group consisting of halogen, hydroxy, amino, nitro, carboxy, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-$S(O)_n$, $(C_1-C_4)$haloalkyl-$S(O)_n$, $(C_1-C_4)$alkylamino, di$[(C_1-C_4)$alkyl]amino, $(C_1-C_4)$alkylcarbonyl, $(C_1-C_4)$alkoxycarbonyl and in the case of heteroaryl also oxo, where heteroaryl in the abovementioned radicals independently of one another in each case is a mono-, bi- or tricyclic heteroaromatic ring system in which at least 1 ring contains one or more hetero atoms (preferably 1, 2 or 3 hetero atoms) selected from the group consisting of N, O and S, and which contains a total of 5 to 14 (preferably 5 to 7) ring atoms wherein at least one ring is fully unsaturated (any further rings being unsaturated, or partially or fully hydrogenated); and heterocyclyl is a heterocyclic radical having 3 to 7 ring atoms and 1 to 3 hetero atoms selected from the group consisting of N, O and S; and $R^{10}$ is H.

A further preferred class of compounds of formula (I) for use in the invention are those in which:

X and Y together with the two carbon atoms to which they are attached form a ring of formula (A) above;

Q, T, W and V are each $CR^{11}$;

$R^1$ is H, halogen or $(C_1-C_6)$alkoxy;

$R^{10}$ is H; and $R^{11}$ is H, halogen, nitro, cyano, sulfamoyl, $(C_1-C_6)$alkyl or $(C_1-C_6)$haloalkyl.

A further preferred class of compounds of formula (I) for use in the invention are those in which:

X is H;

Y is OH; and $R^1$ is H, halogen or $(C_1-C_6)$alkoxy.

A further preferred class of compounds of formula (I) for use in the invention are those in which:

X is $CO_2R^2$;

Y is OH;

$R^1$ is H, halogen or $(C_1-C_6)$alkoxy; and $R^2$ is $(C_1-C_6)$alkyl.

A further preferred class of compounds of formula (I) for use in the invention are those in which:

X is H;

Y is $NHNHR^3$, $R^1$ is H, halogen or $(C_1-C_6)$alkoxy; and $R^3$ is phenyl substituted by halogen; or pyrazolyl substituted by one or more radicals selected from the group consisting of $(C_1-C_6)$alkyl and nitro; or pyridyl substituted by one or more radicals selected from the group consisting of halogen and $(C_1-C_6)$haloalkyl; or benzothiazolyl.

A further preferred class of compounds of formula (I) for use in the invention are those in which:

X is H;

Y is $NHNHC(=S)NHR^6$ or;

$R^1$ is H or $(C_1-C_6)$alkoxy; and $R^6$ is $(C_1-C_6)$alkyl.

Compounds of formula (I) above may be prepared by the application or adaptation of known methods (i.e. methods heretofore used or described in the literature).

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the invention compounds of formula (I) wherein X is $CO_2R^2$, Y is OH and $R^1$ is as defined above, may be prepared by the cyclisation of a compound of formula (II):

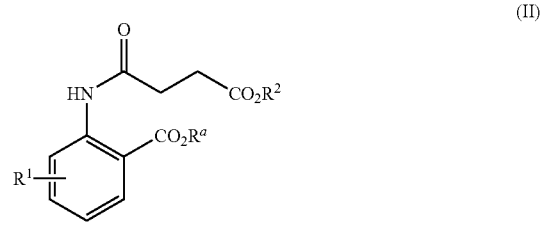

(II)

wherein $R^1$ and $R^2$ are as defined above and $R^a$ is $(C_1-C_6)$ alkyl, preferably methyl or ethyl, using a strong base. The reaction is generally performed in an inert solvent such as N,N-dimethylformamide and/or toluene, at a temperature of from −20° C. to 100° C., preferably from −10° C. to 80° C. The preferred base is an alkali metal hydride such as sodium hydride or potassium hydride, or an alkali metal alkoxide such as potassium tert-butoxide. The amount of base used is typically from 2 to 5 molar equivalents, preferably from 2 to 3 molar equivalents.

According to a further feature of the invention compounds of formula (I) wherein X is H, Y is OH and $R^1$ is as defined above, may be prepared by the hydrolysis-decarboxylation reaction of a compound of formula (II). The hydrolysis-decarboxylation is generally carried out by heating in a solvent such as dimethylsulfoxide and water at a temperature of from 80° C. to 200° C., preferably from 120° C. to 170° C.

According to a further feature of the invention compounds of formula (I) wherein X and Y together with the two carbon atoms to which they are attached form a ring of formula (A) as defined above, and $R^1$, $R^{10}$, Q, T, W and V are as defined above, may be prepared by the reaction of a compound of formula (I) wherein X is $CO_2R^2$, Y is OH and $R^1$ is as defined above, with a hydrazine compound of formula (III):

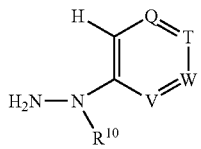

(III)

wherein $R^{10}$ is as defined above, to give the corresponding hydrazone derivative of formula (Ia):

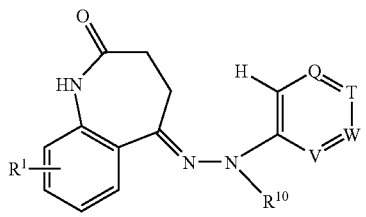

(Ia)

followed by the Fischer ring closure reaction to give the compound of formula (Ib):

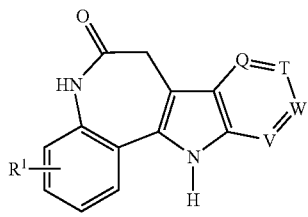

(Ib)

The formation of the hydrazone (Ia) is generally performed in a solvent such as acetic acid at a temperature of from 50° C. to 100° C., using either the hydrazine of formula (III) or an acid salt thereof such as the hydrochloride salt in the presence of a weak base such as sodium acetate. The hydrazone may be isolated or used directly in the Fischer reaction, which is generally performed by heating with a strong acid preferably sulfuric acid, in a solvent such as acetic acid, at a temperature of from 50° C. to 100° C.

Compounds of formula (I) wherein X is $CO_2R^2$ or H; Y is $NHNR^3R^4$, $NHNHC(=Z)NR^5R^6$ or $NHNHC(=Z)CR^7R^8R^9$, and $R^1$ is as defined above, may be prepared by the reaction of the corresponding compound of formula (I) wherein X is $CO_2R^2$ or H; Y is OH and $R^1$ is as defined above, with a hydrazine compound of formula (IV), (V) or (VI):

 (IV)

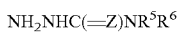 (V)

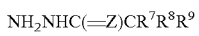 (VI)

The reaction is generally carried out by the same procedure described above for the preparation of hydrazone compounds of formula (Ia).

Compounds of formula (II), (III), (IV), (V) and (VI) are known or may be prepared according to known methods.

A collection of compounds of formula (I) which can be synthesized by the above-mentioned processes can additionally be prepared in parallel fashion, which can be effected manually, partly automated or fully automated. In this context, it is possible to automate the procedure of the reaction, work-up or purification of the products or intermediates. In total, this is to be understood as meaning a procedure which is described, for example, by S. H. DeWitt in "Annual Reports in Combinatorial Chemistry and Molecular Diversity: Automated Synthesis", Volume 1, published by Escom, 1997, pages 69 to 77.

For carrying out the reaction and work-up in parallel fashion, a series of commercially available apparatuses can be used as they are available from, for example, Stem Corporation, Woodrolfe Road, Tollesbury, Essex, CM9 8SE, England or Radleys Discovery Technologies, Saffron Walden, Essex, CB11 3AZ, ENGLAND. To carry out the parallel purification of compounds (I) or of intermediates obtained during the preparation, there are available, inter alia, chromatographic equipment, for example from ISCO, Inc., 4700 Superior Street, Lincoln, Nebr. 68504, USA. The equipment mentioned makes possible a modular procedure, where the individual steps are automated, but manual operation has to be carried out between the steps. This can be circumvented by employing partly or fully integrated automation systems, in which the automation modules in question are operated by, for example, robots. Such automation systems can be obtained from, for example, Zymark Corporation, Zymark Center, Hopkinton, Mass. 01748, USA.

In addition to the above-described methods, compounds of formula (I) can be prepared in full or partly by solid-phase supported methods. To this end, individual intermediates or all intermediates of the synthesis or of a synthesis adapted to the procedure in question are bound to a synthesis resin. Solid-phase supported synthetic methods are described extensively in the specialist literature, for example: Barry A. Bunin in "The Combinatorial Index", published by Academic Press, 1998. The use of solid-phase supported synthesis methods permits a series of protocols known from the literature which, in turn, can be carried out manually or in an automated fashion. For example, the "teabag method" (Houghten, U.S. Pat. No. 4,631,211; Houghten et al., Proc. Natl. Acad. Sci., 1985, 82, 5131-5135) can be partly automated with products of IRORI, 11149 North Torrey Pines Road, La Jolla, Calif. 92037, USA. Solid-phase supported parallel synthesis can be automated successfully for example using equipment by Argonaut Technologies, Inc., 887 Industrial Road, San Carlos, Calif. 94070, USA or MultiSynTech GmbH, Wullener Feld 4, 58454 Witten, Germany.

The preparation in accordance with the processes described herein yields compounds of formula (I) in the form of substance collections or substance libraries. Subject matter of the present invention are therefore also libraries of the compounds of formula (I) which contain at least two compounds of formula (I), and of their precursors.

The following non-limiting Examples illustrate the preparation of the compounds of formula (I).

A. CHEMICAL EXAMPLES

Example 1

5-Hydroxy-7,8-dimethoxy-2-oxo-2,3-dihydro-1H-benzo[b]azepine-4-carboxylic acid ethyl ester (Compound 2.4)

A solution of 4,5-dimethoxy-2-[(4-ethoxy-1,4-dioxobutyl)amino]benzoic acid ethyl ester (5.940 g, 16 mmol) and N,N-dimethylformamide (7.5 ml) in toluene (60 ml) was added dropwise to a stirred suspension of powdered sodium hydride (80%, 2.57 g, 85.7 mmol) under argon in toluene (70 ml). After the hydrogen evolution had ceased, the mixture was stirred for 7 hours at 80° C. under argon, then cooled to 20° C. and acetic acid (5 ml) and water (40 ml) added dropwise in succession. Brine (100 ml) was added and the organic phase dried (magnesium sulphate) and evaporated to give the title compound as a white solid, (2.842 g, 55% yield), mp 218° C.; 1H-NMR (DMSO-d6, 300 MHz): δ (ppm)=12.7 (br s; 1 H), 7.96 (s; 1H), 7.3 (s; 1H), 6.49 (s; 1H), 4.32 (q; 2H), 3.95 and 3.93 (s; 6H), 3.1 (s; 2H), 1.38 (t; 3H).

Example 2

7,8-Dimethoxy-1H-benzazepine-2,5 (3H, 4H)-dione (Compound 3.2)

A solution of 2,3-dihydro-7,8-dimethoxy-5-hydroxy-2-oxo-1H-[1]-benzazepine-4-carboxylic acid ethyl ester (0.614 g, 1.9 mmol) and water (1 ml) in dimethylsulfoxide (20 ml) was stirred at 150° C. under argon. Portions of water (1 ml) were added after 1 hour and 3 hours heating. After stirring for a total of 6 hours at 150° C., the mixture was cooled to 20° C., poured into ice cold water (20 ml) and allowed to stand overnight at 4° C. The crystals were filtered off and washed with water and hexanes to give the title compound as yellowish crystals (0.325 g, yield 67.7%), mp 230° C.; 1H-NMR (DMSO-d6, 300 MHz): δ (ppm)=8.42 (s; 1H), 7.5 (s; 1H), 6.43 (s; 1H), 3.96 and 3.92 (s; 6H), 2.90 (m, 2H), 2.8 (m; 2H).

Example 3

9-Bromo-7,12-dihydroindolo[3,2-d][1]-benzazepin-6 (5H)-one (Compound 1.2)

To a suspension of 1H-[1]benzazepin-2,5(3H, 4H)-dione (0.247 g, 1.3 mmol) in acetic acid (5 ml) was added 4-bromophenylhydrazine hydrochloride (0.532 g, 2.3 mmol) and sodium acetate (0.195 g, 2.3 mmol) and stirred under argon. The mixture was heated at 70° C. for 3 hours, then cooled and concentrated sulfuric acid (0.5 ml) added, before heating at 70° C. for a further 3 hours. The slurry was poured into 10% sodium acetate aqueous solution (20 ml) and the precipitate filtered to give the title compound as a cream solid (0.367 g, yield 79.6%), mp>300° C.; 1H-NMR (DMSO-d6, 300 MHz): δ (ppm)=11.82 (s; 1 H), 10.1 (s; 1H), 7.89 (d; 1H), 7.74 (dd; 1H), 7.41-7.36 (m; 2H), 7.30-7.21 (m; 3H), 3.51 (s; 2H).

Example 4

5-[(1,3-Dimethyl-4-nitro-1H-pyrazol-5-yl)hydrazono]-7,8-dimethoxy-1,3,4,5-tetrahydro-benzo[b]azepin-2-one (Compound 4.2)

1,3-Dimethyl-4-nitro-1H-pyrazol-5-yl-hydrazine (0.073 g, 0.4 mmol) was added to a suspension of 7,8-dimethoxy-1H-[1]benzazepin-2,5(3H, 4H)-dione (0.100 g, 0.4 mmol) in acetic acid (5 ml) with stirring under argon. The mixture was heated at 70° C. for 2 days, cooled and water (5 ml) added. The precipitate was then filtered off to give the title compound as a yellow solid (0.019 g, yield 11.5%); 1H-NMR (DMSO-d6, 300 MHz): δ (ppm)=12.8 (v br s; 1 H), 9.59 (s; 1H), 7.2 (s; 1H), 6.63 (s; 1H), 3.96 (s; 3H), 3.75-3.77 (s, 6H), 3.05 (br t, 2H), 2.57 (br t, 2H), 2.35 (s, 3H).

The following Intermediate Example illustrates the preparation of intermediates used in the synthesis of the above Examples.

Intermediate Example 1

4,5-Dimethoxy-2-[(4-ethoxy-1,4-dioxobutyl)amino]benzoic acid ethyl ester

A solution of ethyl succinyl chloride (1.284 g, 5.7 mmol) in toluene (15 ml) was added dropwise to a cooled solution of 2-amino-4,5-dimethoxybenzoic acid ethyl ester (1.240 g, 7.4 mmol) and pyridine (0.67 ml) in toluene (1 ml) with stirring under nitrogen. The resulting suspension was stirred for 4 hours at 20° C. and water (13 ml) and dichloromethane then added. The organic phase was washed with hydrochloric acid (10%) and aqueous sodium carbonate solution (5%), dried (sodium sulfate) and evaporated. The residue was crystallised from ethanol to yield the title compound (1.42 g, yield 70%) as colourless crystals, mp 125° C.; 1H-NMR (DMSO-d6, 300 MHz): δ (ppm)=11.26 (br s; 1 H), 8.43 (s; 1H), 7.46 (s; 1H), 4.39 (q, 2H), 4.18 (q, 2H), 3.92 (s, 3H), 3.87 (s; 3H), 2.75 (m; 4H), 1.42 (t, 3H), 1.23 (t, 3H).

The following compounds of formula (I) shown in Tables 1 to 4 are also preferred for use in the present invention, and are obtained by, or analogously to, the above Examples 1 to 4 or the above-described general methods.

The following abbreviations are used in the Tables:

"Cpd" means Compound Number. Compound numbers are given for reference purposes only. "Me" means methyl, "Et" means ethyl, "Ph" means phenyl and "MeO" means methoxy.

"Dec." means the compound decomposes before the melting point.

Rf means retention time determined from thin layer chromatography on silica gel, using 1:1 heptane/ethyl acetate as solvent.

TABLE 1

7,12-Dihydroindolo[3,2-d][1]benzazepin-6(5H)-one compounds of formula (Ic):

(Ic)

| Cpd | $R^{20}$ | $R^{21}$ | $R^{22}$ | $R^{23}$ | $R^{24}$ | $R^{25}$ | mp (° C.) | Rf |
|---|---|---|---|---|---|---|---|---|
| 1.1 | H | H | H | Cl | H | Cl | >300 | 0.48 |
| 1.2 | H | H | H | Br | H | H | >300 | 0.05 |
| 1.3 | MeO | MeO | H | $CF_3$ | H | H | >300 | 0.05 |
| 1.4 | Cl | H | H | Me | Cl | H | >300 | 0.10 |
| 1.5 | Cl | H | H | F | H | H | >300 | 0.10 |
| 1.6 | MeO | MeO | H | Br | H | H | >300 | 0.16 |
| 1.7 | H | H | H | F | H | H | >300 | 0.5 |
| 1.8 | H | H | Cl | H | Cl | H | >300 | 0.51 |
| 1.9 | H | H | H | Cl | Cl | H | >300 | 0.64 |
| 1.10 | H | H | H | Me | Me | H | >300 | 0.62 |
| 1.11 | H | H | H | H | Cl | Cl | >300 | 0.62 |
| 1.12 | H | H | H | $SO_2NH_2$ | H | H | >300 | 0.64 |
| 1.13 | H | H | H | $CF_3$ | H | H | dec. | 0.48 |
| 1.14 | Cl | H | H | Cl | H | H | dec. | 0.6 |
| 1.15 | Br | H | H | Cl | H | Cl | | |
| 1.16 | Br | H | H | Br | H | H | | |
| 1.17 | Br | H | H | $CF_3$ | H | H | | |
| 1.18 | Br | H | H | Me | Cl | H | | |
| 1.19 | Br | H | H | F | H | H | | |
| 1.20 | Br | H | H | Br | H | H | | |
| 1.21 | Br | H | H | F | H | H | | |
| 1.22 | Br | H | Cl | H | Cl | H | | |
| 1.23 | Br | H | H | Cl | Cl | H | | |
| 1.24 | Br | H | H | Me | Me | H | | |
| 1.25 | Br | H | H | H | Cl | Cl | | |
| 1.26 | Br | H | H | $SO_2NH_2$ | H | H | | |
| 1.27 | Br | H | H | $CF_3$ | H | H | | |
| 1.28 | Br | H | H | Cl | H | H | | |
| 1.29 | F | H | H | Cl | H | Cl | | |
| 1.30 | F | H | H | Br | H | H | | |
| 1.31 | F | H | H | $CF_3$ | H | H | | |
| 1.32 | F | H | H | Me | Cl | H | | |
| 1.33 | F | H | H | F | H | H | | |
| 1.34 | F | H | H | Br | H | H | | |
| 1.35 | F | H | H | F | H | H | | |
| 1.36 | F | H | Cl | H | Cl | H | | |
| 1.37 | F | H | H | Cl | Cl | H | | |
| 1.38 | F | H | H | Me | Me | H | | |
| 1.39 | F | H | H | H | Cl | Cl | | |
| 1.40 | F | H | H | $SO_2NH_2$ | H | H | | |
| 1.41 | F | H | H | $CF_3$ | H | H | | |
| 1.42 | F | H | H | Cl | H | H | | |
| 1.43 | $NO_2$ | H | H | Cl | H | Cl | | |
| 1.44 | $NO_2$ | H | H | Br | H | H | | |
| 1.45 | $NO_2$ | H | H | $CF_3$ | H | H | | |
| 1.46 | $NO_2$ | H | H | Me | Cl | H | | |
| 1.47 | $NO_2$ | H | H | F | H | H | | |
| 1.48 | $NO_2$ | H | H | Br | H | H | | |
| 1.49 | $NO_2$ | H | H | F | H | H | | |
| 1.50 | $NO_2$ | H | Cl | H | Cl | H | | |
| 1.51 | $NO_2$ | H | H | Cl | Cl | H | | |
| 1.52 | $NO_2$ | H | H | Me | Me | H | | |
| 1.53 | $NO_2$ | H | H | H | Cl | Cl | | |
| 1.54 | $NO_2$ | H | H | $SO_2NH_2$ | H | H | | |
| 1.55 | $NO_2$ | H | H | $CF_3$ | H | H | | |
| 1.56 | $NO_2$ | H | H | Cl | H | H | | |
| 1.57 | $CF_3$ | H | H | Cl | H | Cl | | |
| 1.58 | $CF_3$ | H | H | Br | H | H | | |
| 1.59 | $CF_3$ | H | H | $CF_3$ | H | H | | |
| 1.60 | $CF_3$ | H | H | Me | Cl | H | | |
| 1.61 | $CF_3$ | H | H | F | H | H | | |
| 1.62 | $CF_3$ | H | H | Br | H | H | | |
| 1.63 | $CF_3$ | H | H | F | H | H | | |
| 1.64 | $CF_3$ | H | Cl | H | Cl | H | | |
| 1.65 | $CF_3$ | H | H | Cl | Cl | H | | |
| 1.66 | $CF_3$ | H | H | Me | Me | H | | |
| 1.67 | $CF_3$ | H | H | H | Cl | Cl | | |
| 1.68 | $CF_3$ | H | H | $SO_2NH_2$ | H | H | | |
| 1.69 | $CF_3$ | H | H | $CF_3$ | H | H | | |
| 1.70 | $CF_3$ | H | H | Cl | H | H | | |
| 1.71 | MeO | H | H | Cl | H | Cl | | |
| 1.72 | MeO | H | H | Br | H | H | | |
| 1.73 | MeO | H | H | $CF_3$ | H | H | | |
| 1.74 | MeO | H | H | Me | Cl | H | | |
| 1.75 | MeO | H | H | F | H | H | | |
| 1.76 | MeO | H | H | Br | H | H | | |
| 1.77 | MeO | H | H | F | H | H | | |
| 1.78 | MeO | H | Cl | H | Cl | H | | |
| 1.79 | MeO | H | H | Cl | Cl | H | | |
| 1.80 | MeO | H | H | Me | Me | H | | |
| 1.81 | MeO | H | H | H | Cl | Cl | | |
| 1.82 | MeO | H | H | $SO_2NH_2$ | H | H | | |
| 1.83 | MeO | H | H | $CF_3$ | H | H | | |
| 1.84 | MeO | H | H | Cl | H | H | | |
| 1.85 | $OCF_3$ | H | H | Cl | H | Cl | | |
| 1.86 | $OCF_3$ | H | H | Br | H | H | | |
| 1.87 | $OCF_3$ | H | H | $CF_3$ | H | H | | |
| 1.88 | $OCF_3$ | H | H | Me | Cl | H | | |
| 1.89 | $OCF_3$ | H | H | F | H | H | | |
| 1.90 | $OCF_3$ | H | H | Br | H | H | | |
| 1.91 | $OCF_3$ | H | H | F | H | H | | |
| 1.92 | $OCF_3$ | H | Cl | H | Cl | H | | |
| 1.93 | $OCF_3$ | H | H | Cl | Cl | H | | |
| 1.94 | $OCF_3$ | H | H | Me | Me | H | | |
| 1.95 | $OCF_3$ | H | H | H | Cl | Cl | | |
| 1.96 | $OCF_3$ | H | H | $SO_2NH_2$ | H | H | | |
| 1.97 | $OCF_3$ | H | H | $CF_3$ | H | H | | |
| 1.98 | $OCF_3$ | H | H | Cl | H | H | | |
| 1.99 | $CHF_2$ | H | H | Cl | H | Cl | | |
| 1.100 | $CHF_2$ | H | H | Br | H | H | | |
| 1.101 | $CHF_2$ | H | H | $CF_3$ | H | H | | |
| 1.102 | $CHF_2$ | H | H | Me | Cl | H | | |
| 1.103 | $CHF_2$ | H | H | F | H | H | | |
| 1.104 | $CHF_2$ | H | H | Br | H | H | | |
| 1.105 | $CHF_2$ | H | H | F | H | H | | |
| 1.106 | $CHF_2$ | H | Cl | H | Cl | H | | |
| 1.107 | $CHF_2$ | H | H | Cl | Cl | H | | |
| 1.108 | $CHF_2$ | H | H | Me | Me | H | | |
| 1.109 | $CHF_2$ | H | H | H | Cl | Cl | | |
| 1.110 | $CHF_2$ | H | H | $SO_2NH_2$ | H | H | | |
| 1.111 | $CHF_2$ | H | H | $CF_3$ | H | H | | |
| 1.112 | $CHF_2$ | H | H | Cl | H | H | | |

TABLE 2

5-Hydroxy-2-oxo-2,3-dihydro-1H-[1]benzazepine-4-carboxylic acid ethyl ester compounds of formula (Id):

(Id)

| Cpd | $R^{20}$ | $R^{21}$ | mp (° C.) | Rf |
|---|---|---|---|---|
| 2.1 | H | H | 207 | 0.8 |
| 2.2 | Br | H | 200 | 0.83 |
| 2.3 | Cl | H | dec. | 0.5 |
| 2.4 | MeO | MeO | 218 | 0.13 |
| 2.5 | F | H | | |
| 2.6 | H | F | | |
| 2.7 | MeO | H | | |

TABLE 3

2,3-Dihydro-1H-[1]benzazepine-4H-2,5-dione compounds of formula (Ie):

(Ie)

| Cpd | $R^{20}$ | $R^{21}$ | mp (° C.) | Rf |
|---|---|---|---|---|
| 3.1 | H | H | 182 | 0.09 |
| 3.2 | MeO | MeO | 230 | 0.07 |
| 3.3 | Br | H | 209 | 0.04 |
| 3.4 | Cl | H | 208 | 0.16 |
| 3.5 | F | H | | |
| 3.6 | $CCl_2H$ | H | | |
| 3.7 | $CF_3$ | H | | |
| 3.8 | $CHF_2$ | H | | |
| 3.9 | CN | H | | |
| 3.10 | $NO_2$ | H | | |
| 3.11 | Me | H | | |

TABLE 4

2,3-Dihydro-2-oxo-1H-[1]benzazepine-4H-5-hydrazone compounds of formula (If):

(If)

| Cpd | $R^{20}$ | $R^{21}$ | $=N-NR^3R^4$ | mp (° C.) | Rf |
|---|---|---|---|---|---|
| 4.1 | Br | H | =N—NH-(3,5-$Cl_2$Ph) | >300 | 0.10 |
| 4.2 | MeO | MeO | =N—NH-(1,3-$Me_2$-4-$NO_2$-1H-pyrazol-5-yl) | dec. | 0.12 |
| 4.3 | MeO | MeO | =N—NH-(3-Cl-5-$CF_3$-pyrid-2-yl) | dec. | 0.18 |
| 4.4 | Br | H | =N—NH-(benzothiazol-2-yl) | dec. | 0.1 |
| 4.5 | MeO | MeO | =N—NH—C(=S)NHEt | dec. | 0.16 |
| 4.6 | F | H | =N—NH-(3,5-$Cl_2$Ph) | | |
| 4.7 | F | H | =N—NH-(1,3-$Me_2$-4-$NO_2$-1H-pyrazol-5-yl) | | |
| 4.8 | F | H | =N—NH-(3-Cl-5-$CF_3$-pyrid-2-yl) | | |
| 4.9 | F | H | =N—NH-(benzothiazol-2-yl) | | |
| 4.10 | F | H | =N—NH—C(=S)NHEt | | |
| 4.11 | Cl | H | =N—NH-(3,5-$Cl_2$Ph) | | |
| 4.12 | Cl | H | =N—NH-(1,3-$Me_2$-4-$NO_2$-1H-pyrazol-5-yl) | | |
| 4.13 | Cl | H | =N—NH-(3-Cl-5-$CF_3$-pyrid-2-yl) | | |
| 4.14 | Cl | H | =N—NH-(benzothiazol-2-yl) | | |
| 4.15 | Cl | H | =N—NH—C(=S)NHEt | | |
| 4.16 | Me | H | =N—NH-(3,5-$Cl_2$Ph) | | |
| 4.17 | Me | H | =N—NH-(1,3-$Me_2$-4-$NO_2$-1H-pyrazol-5-yl) | | |

TABLE 4-continued 2,3-Dihydro-2-oxo-1H-[1]benzazepine-4H-5-hydrazone compounds of formula (If):

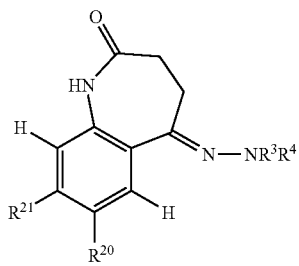

(If)

| Cpd | $R^{20}$ | $R^{21}$ | $=N-NR^3R^4$ | mp (° C.) | Rf |
|---|---|---|---|---|---|
| 4.18 | Me | H | $=N-NH$-(3-Cl-5-$CF_3$-pyrid-2-yl) | | |
| 4.19 | Me | H | $=N-NH$-(benzothiazol-2-yl) | | |
| 4.20 | Me | H | $=N-NH-C(=S)NHEt$ | | |

Another aspect of the invention is a method for plant growth regulation which plants are monocotyledoneous or dicotyledoneous crop plants, or parts thereof, preferably selected from the group of economically important field crops such as, for example wheat, barley, rye, triticale, rice, maize, sugar beet, cotton, or soybeans, particularly maize, wheat, and soybean, as well as vegetables and ornamentals, said method comprising applying to said plants, to the seeds from which they grow or to the locus in which they grow, a non-phytotoxic, effective plant growth regulating amount of one or more compounds of formula (I), optionally in mixture with carriers and/or surfactants, and further optionally in mixture with a further active compound selected from the group consisting of acaricides, fungicides, herbicides, insecticides, nematicides or plant growth regulating substances not identical to compounds defined by formula (I).

In case that it is intended to apply the compound having formula (I) either alone or together with a further active compound directly to the seed, there are several ways on how to perform such seed treatment, like by "filmcoating" which is characterized by the creation of a liquid formulation containing an applicable polymer which will be applied to the seed, thereby improving the adherence, the coverage and the distribution of the compounds on the seed.

Among the further active compounds to be applied together with a compound having the formula (I), either applied as one further active compound or applied in a combination of several further active compounds, the following compounds are specifically named as examples of such further active compounds: 2-Phenylphenol; 8-Hydroxyquinoline sulfate; Acibenzolar-S-methyl; Actinovate; Aldimorph; Amidoflumet; Ampropylfos; Ampropylfos-potassium; Andoprim; Anilazine; Azaconazole; Azoxystrobin; Benalaxyl; Benodanil; Benomyl; Benthiavalicarbisopropyl; Benzamacril; Benzamacril-isobutyl; Bilanafos; Binapacryl; Biphenyl; Bitertanol; Blasticidin-S; Boscalid; Bromuconazole; Bupirimate; Buthiobate; Butylamine; Calcium polysulfide; Capsimycin; Captafol; Captan; Carbendazim; Carboxin; Carpropamid; Carvone; Chinomethionat; Chlobenthiazone; Chlorfenazole; Chloroneb; Chlorothalonil; Chlozolinate; cis-1-(4-chlorophenyl)-2-(1H-1,2,4-triazole-1-yl)-cycloheptanol; Clozylacon; Cyazofamid; Cyflufenamid; Cymoxanil; Cyproconazole; Cyprodinil; Cyprofuram; Dagger G; Debacarb; Dichlofluanid; Dichlone; Dichlorophen; Diclocymet; Diclomezine; Dicloran; Diethofencarb; Difenoconazole; Diflumetorim; Dimethirimol; Dimethomorph; Dimoxystrobin; Diniconazole; Diniconazole-M; Dinocap; Diphenylamine; Dipyrithione; Ditalimfos; Dithianon; Dodine; Drazoxolon; Edifenphos; Epoxiconazole; Ethaboxam; Ethirimol; Etridiazole; Famoxadone; Fenamidone; Fenapanil; Fenarimol; Fenbuconazole; Fenfuram; Fenhexamid; Fenitropan; Fenoxanil; Fenpiclonil; Fenpropidin; Fenpropimorph; Ferbam; Fluazinam; Flubenzimine; Fludioxonil; Flumetover; Flumorph; Fluoromide; Fluoxastrobin; Fluquinconazole; Flurprimidol; Flusilazole; Flusulfamide; Flutolanil; Flutriafol; Folpet; Fosetyl-Al; Fosetyl-sodium; Fuberidazole; Furalaxyl; Furametpyr; Furcarbanil; Furmecyclox; Guazatine; Hexachlorobenzene; Hexaconazole; Hymexazol; Imazalil; Imibenconazole; Iminoctadine triacetate; Iminoctadine tris(albesilate); Iodocarb; Ipconazole; Iprobenfos; Iprodione; Iprovalicarb; Irumamycin; Isoprothiolane; Isovaledione; Kasugamycin; Kresoximmethyl; Mancozeb; Maneb; Meferimzone; Mepanipyrim; Mepronil; Metalaxyl; Metalaxyl-M; Metconazole; Methasulfocarb; Methfuroxam; methyl 1-(2,3-dihydro-2,2-dimethyl-1H-inden-1-yl)-1H-imidazole-5-carboxylate; Methyl 2-[[[cyclopropyl[(4-methoxyphenyl)imino]methyl]thio]methyl]-.alpha.-(methoxymethylene)-benzeneacetate; Methyl 2-[2-[3-(4-chloro-phenyl)-1-methyl-allylideneaminooxymethyl]-phenyl]-3-methoxy-acrylate; Metiram; Metominostrobin; Metrafenone; Metsulfovax; Mildiomycin; monopotassium carbonate; Myclobutanil; Myclozolin; N-(3-Ethyl-3,5,5-trimethyl-cyclohexyl)-3-formylamino-2-hydroxy-benzamide; N-(6-methoxy-3-pyridinyl)-cyclopropanecarboxamide; N-butyl-8-(1,1-dimethylethyl)-1-oxaspiro[4.5]decan-3-amine; Natamycin; Nitrothal-isopropyl; Noviflumuron; Nuarimol; Ofurace; Orysastrobin; Oxadixyl; Oxolinic acid; Oxpoconazole; Oxycarboxin; Oxyfenthiin; Paclobutrazol; Pefurazoate; Penconazole; Pencycuron; Penthiopyrad; Phosdiphen; Phthalide; Picobenzamid; Picoxystrobin; Piperalin; Polyoxins; Polyoxorim; Probenazole; Prochloraz; Procymidone; Propamocarb; Propanosine-sodium; Propiconazole; Propineb; Proquinazid; Prothioconazole; Pyraclostrobin; Pyrazophos; Pyrifenox; Pyrimethanil; Pyroquilon; Pyroxyfur; Pyrrolnitrine; Quinconazole; Quinoxyfen; Quintozene; Silthiofam; Simeconazole; Sodium tetrathiocarbonate; Spiroxamine; Sulfur; Tebuconazole; Tecloftalam; Tecnazene; Tetcyclacis; Tetraconazole; Thiabendazole; Thicyofen; Thifluzamide; Thiophanate-methyl; Thiram; Tiadinil; Tioxymid; Tolclofos-methyl; Tolylfluanid; Triadimefon; Triadimenol; Triazbutil; Triazoxide; Tricyclamide; Tricyclazole; Tridemorph; Trifloxystrobin; Triflumizole; Triforine; Triticonazole; Uniconazole; Validamycin A; Vinclozolin; Zineb; Ziram; Zoxamide; (2S)—N-[2-[4-[[3-(4-chlorophenyl)-2-propynyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl)-pyridine; 2,4-Dihydro-5-methoxy-2-methyl-4-[[[[[1-[3-(trifluoromethyl)-phenyl]-ethylidene]-amino]-oxy]-methyl]-phenyl]-3H-1,2,3-triazol-3-one; 2-amino-4-methyl-N-phenyl-5-thiazolecarboxamide; 2-chloro-N-(2,3-dihydro-1,1,3-trimethyl-1H-inden-4-yl)-3-pyridincarboxamide; 3,4,5-trichloro-2,6-pyridinedicarbonitrile; 3-[(3-Bromo-6-fluoro-2-methyl-1H-indol-1-yl)sulfonyl]-N,N-dimethyl-1H-1,2,4-triazole-1-sulfonamide;

Copper salts and Copper preparations, like Bordeaux mixture; Copper hydroxide; Copper naphthenate; Copper oxychloride; Copper sulfate; Cufraneb; Cuprous oxide; Mancopper; Oxine-copper; Alanycarb, Aldicarb, Aldoxycarb, Allyxycarb, Aminocarb, Bendiocarb, Benfuracarb, Bufencarb, Butacarb, Butocarboxim, Butoxycarboxim, Carbaryl, Carbofuran, Carbosulfan, Cloethocarb, Dimetilan, Ethiofencarb, Fenobucarb, Fenothiocarb, Formetanate, Furathiocarb, Isoprocarb, Metam-sodium, Methiocarb, Methomyl, Metolcarb, Oxamyl, Pirimicarb, Promecarb, Propoxur, Thiodicarb, Thiofanox, Trimethacarb, XMC, Xylylcarb, Acephate, Azamethiphos, Azinphos (-methyl, -ethyl), Bromophosethyl, Bromfenvinfos (-methyl), Butathiofos, Cadusafos, Carbophenothion, Chlorethoxyfos, Chlorfenvinphos, Chlormephos, Chlorpyrifos (-methyl/-ethyl), Coumaphos, Cyanofenphos, Cyanophos, Chlorfenvinphos, Demeton-5-methyl, Demeton-5-methylsulphon, Dialifos, Diazinon, Dichlofenthion, Dichlorvos/DDVP, Dicrotophos, Dimethoate, Dimethylvinphos, Dioxabenzofos, Disulfoton, EPN, Ethion, Ethoprophos, Etrimfos, Famphur, Fenamiphos, Fenitrothion, Fensulfothion, Fenthion, Flupyrazofos, Fonofos, Formothion, Fosmethilan, Fosthiazate, Heptenophos, Iodofenphos, Iprobenfos, Isazofos, Isofenphos, Isopropyl O-salicylate, Isoxathion, Malathion, Mecarbam, Methacrifos, Methamidophos, Methidathion, Mevinphos, Monocrotophos, Naled, Omethoate, Oxydemeton-methyl, Parathion (-methyl/-ethyl), Phenthoate, Phorate, Phosalone, Phosmet, Phosphamidon, Phosphocarb, Phoxim, Pirimiphos (-methyl/-ethyl), Profenofos, Propaphos, Propetamphos, Prothiofos, Prothoate, Pyraclofos, Pyridaphenthion, Pyridathion, Quinalphos, Sebufos, Sulfotep, Sulprofos, Tebupirimfos, Temephos, Terbufos, Tetrachlorvinphos, Thiometon, Triazophos, Triclorfon, Vamidothion, Acrinathrin, Allethrin (d-cis-trans, d-trans), Beta-Cyfluthrin, Bifenthrin, Bioallethrin, Bioallethrin-S-cyclopentyl-isomer, Bioethanomethrin, Biopermethrin, Bioresmethrin, Chlovaporthrin, Cis-Cypermethrin, Cis-Resmethrin, Cis-Permethrin, Clocythrin, Cycloprothrin, Cyfluthrin, Cyhalothrin, Cypermethrin (alpha-, beta-, theta-, zeta-), Cyphenothrin, Deltamethrin, Empenthrin (1R-isomer), Esfenvalerate, Etofenprox, Fenfluthrin, Fenpropathrin, Fenpyrithrin, Fenvalerate, Flubrocythrinate, Flucythrinate, Flufenprox, Flumethrin, Fluvalinate, Fubfenprox, Gamma-Cyhalothrin, Imiprothrin, Kadethrin, Lambda-Cyhalothrin, Metofluthrin, Permethrin (cis-, trans-), Phenothrin (1R-trans isomer), Prallethrin, Profluthrin, Protrifenbute, Pyresmethrin, Resmethrin, RU 15525, Silafluofen, Tau-Fluvalinate, Tefluthrin, Terallethrin, Tetramethrin (-1R-isomer), Tralomethrin, Transfluthrin, ZXI 8901, Pyrethrins (pyrethrum), DDT, Indoxacarb, Acetamiprid, Clothianidin, Dinotefuran, Imidacloprid, Nitenpyram, Nithiazine, Thiacloprid, Thiamethoxam, Nicotine, Bensultap, Cartap, Camphechlor, Chlordane, Endosulfan, Gamma-HCH, HCH, Heptachlor, Lindane, Methoxychlor Spinosad, Acetoprole, Ethiprole, Fipronil, Vaniliprole, Avermectin, Emamectin, Emamectinbenzoate, Ivermectin, Milbemycin, Diofenolan, Epofenonane, Fenoxycarb, Hydroprene, Kinoprene, Methoprene, Pyriproxifen, Triprene, Chromafenozide, Halofenozide, Methoxyfenozide, Tebufenozide, Bistrifluoron, Chlofluazuron, Diflubenzuron, Fluazuron, Flucycloxuron, Flufenoxuron, Hexaflumuron, Lufenuron, Novaluron, Noviflumuron, Penfluoron, Teflubenzuron, Triflumuron, Buprofezin, Cyromazine, Diafenthiuron, Azocyclotin, Cyhexatin, Fenbutatin-oxide, Chlorfenapyr, Binapacyrl, Dinobuton, Dinocap, DNOC, Fenazaquin, Fenpyroximate, Pyrimidifen, Pyridaben, Tebufenpyrad, Tolfenpyrad, Hydramethylnon, Dicofol, Rotenone, Acequinocyl, Fluacrypyrim, *Bacillus thuringiensis* strains, Spirodiclofen, Spiromesifen, 3-(2,5-Dimethylphenyl)-8-methoxy-2-oxo-1-azaspiro[4.5]dec-3-en-4-yl ethyl carbonate (alias: Carbonic acid, 3-(2,5-dimethylphenyl)-8-methoxy-2-oxo-1-azaspiro[4.5]dec-3-en-4-yl ethyl ester, CAS-Reg.-No.: 382608-10-8) and Carbonic acid, cis-3-(2,5-dimethylphenyl)-8-methoxy-2-oxo-1-azaspiro[4.5]dec-3-en-4-yl ethyl ester (CAS-Reg.-No.: 203313-25-1), Flonicamid, Amitraz, Propargite, N2-[1,1-Dimethyl-2-(methylsulfonyl) ethyl]-3-iodo-N1-[2-methyl-4-[1,2,2,2-tetrafluoro-1-(trifluoromethyl)ethyl]phenyl]-1,2-benzenedicarboxamide (CAS-Reg.-No.: 272451-65-7), Thiocyclam hydrogen oxalate, Thiosultap-sodium, Azadirachtin, *Bacillus* spec., *Beauveria* spec., Codlemone, *Metarrhizium* spec., *Paecilomyces* spec., Thuringiensin, *Verticillium* spec., Aluminium phosphide, Methyl bromide, Sulfuryl fluoride, Cryolite, Flonicamid, Pymetrozine, Clofentezine, Etoxazole, Hexythiazox, Amidoflumet, Benclothiaz, Benzoximate, Bifenazate, Bromopropylate, Buprofezin, Chinomethionat, Chlordimeform, Chlorbenzilate, Chloropicrin, Clothiazoben, Cycloprene, Dicyclanil, Fenoxacrim, Fentrifanil, Flubenzimine, Flufenerim, Flutenzin, Gossyplure, Hydramethylnone, Japonilure, Metoxadiazone, Petroleum, Piperonyl butoxide, Potassium oleate, Pyridalyl, Sulfluramid, Tetradifon, Tetrasul, Triarathene, Verbutin.

Another aspect of the invention is a method for growth regulation in plant tissue cultures of monocotyledoneous or dicotyledoneous plants said method comprising applying to plant tissue cultures an appropriate amount of a compound having the formula (I) either alone or together with at least one further active compound selected from the group of plant growth regulators or plant hormones.

The compounds of formula (I) can preferably be employed as plant growth regulators in crops of useful monocotyledoneous or dicotyledoneous crop plants, preferably selected from the group of economically important field crops such as, for example wheat, barley, rye, triticale, rice, maize, sugar beet, cotton, or soybeans, particularly maize, wheat, and soybean, as well as vegetables and ornamentals, that have been rendered thus by means of genetic engineering.

Traditional ways of generating novel plants which have modified characteristics in comparison with existing plants consist, for example, in traditional breeding methods and the generation of mutants. However, it is also possible to generate novel plants with altered characteristics with the aid of genetic engineering methods (see, for example, EP-A-0221044, EP-A-0131624). For example, several cases have been described of genetic engineering modifications of crop plants with the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659), transgenic crop plants, for example cotton, which are capable of producing Bacillus thuringiensis toxins (Bt toxins) which make the plants resistant to specific pests (EP-A-0142924, EP-A-0193259), transgenic crop plants whose fatty acid spectrum is modified (WO 91/13972).

A large number of techniques in molecular biology by means of which novel transgenic plants with altered characteristics can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423-431).

In order to perform such genetic engineering manipulations, nucleic acid molecules may be introduced into plasmids which allow mutagenesis or a sequence change by means of recombination of DNA sequences. It is possible, for example, with the aid of the abovementioned standard methods to perform base exchanges, to remove subsequences or to add natural or synthetic sequences. To connect the DNA fragments to each other, adaptors or linkers may be attached to the fragments.

For example, plant cells with a reduced activity of a gene product can be generated by expressing at least one corresponding antisense RNA, a sense RNA to achieve a cosuppressory effect or by expressing at least one ribozyme of suitable construction which specifically cleaves transcripts of the abovementioned gene product.

To this end it is possible to make use of, on the one hand, DNA molecules which encompass the entire coding sequence of a gene product inclusive of any flanking sequences which may be present, on the other hand DNA molecules which only encompass parts of the coding sequence, but these parts must be long enough in order to effect, in the cells, an antisense effect. Use may also be made of DNA sequences which show a high degree of homology to the coding sequences of a gene product, but which are not completely identical.

When nucleic acid molecules are expressed in plants, the protein which has been synthesized may be located in any desired compartment of the plant cell. However, to achieve localization in a particular compartment, it is possible, for example, to link the coding region with DNA sequences which guarantee localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells may be regenerated by known techniques to give complete plants. In principle, the transgenic plants can be plants of any desired plant species, that is to say monocotyledonous and also dicotyledonous plants.

This allows transgenic plants to be obtained which exhibit altered characteristics by means of overexpression, suppression or inhibition of homologous (=natural) genes or gene sequences or by means of expression of heterologous (=foreign) genes or gene sequences.

The compounds of formula (I) can preferably be employed in transgenic crops which are resistant to herbicides from the group of the sulfonylureas, glufosinate-ammonium or glyphosate-isopropylammonium and analogous active substances or in analogous showing altered phenotypes, like but not limited to features as for content modification, altered flowering time, male or female sterile plants, environmentally resistant plants due to expression or repression of endogenous or exogeneous genes in the transgenic crop.

The use according to the invention for plant growth regulation also includes the case where the compounds of formula (I) are only formed in the plant or the soil from a precursor ("prodrug") after its application to the plant.

The compounds of formula (I) can be employed in the conventional preparations as wettable powders, emulsifiable concentrates, sprayable solutions, dusts or granules. The invention therefore also relates to plant growth regulating compositions which comprise compounds of formula (I).

According to a further feature of the present invention, there is provided a plant growth regulating composition comprising an effective amount of a compound of formula (I) as defined above or an agriculturally acceptable salt thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of the invention]. The term "homogeneously dispersed" is used to include compositions in which the compounds of formula (I) are dissolved in other components. The term "growth regulating composition" is used in a broad sense to include not only compositions which are ready for use as herbicides but also concentrates which must be diluted before use (including tank mixtures).

The compounds of formula (I) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. HauserVerlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Based on these formulations, it is also possible to prepare combinations with pesticidally active substances such as, for example, insecticides, acaricides, herbicides, fungicides, and with safeners, fertilizers and/or growth regulators, for example in the form of a ready mix or a tank mix.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of compounds of formula (I).

The concentration of compounds of formula (I) in wettable powders is, for example, approximately 10 to 90% by weight, the remainder to 100% by weight being composed of customary formulation components. In the case of emulsifiable concentrates, the concentration of compounds of formula (I) can amount to approximately 1 to 90, preferably 5 to 80% by weight. Formulations in the form of dusts usually comprise 1 to 30% by weight of compounds of formula (I), preferably in most cases 5 to 20% by weight of compounds of formula (I), while sprayable solutions comprise approximately 0.05 to 80, preferably 2 to 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise between 1 and 95% by weight of active substance, preferably between 10 and 80% by weight.

In addition, the formulations of compounds of formula (I) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Suitable formulations for plant growth regulating compositions are known. A description of suitable formulations which may be used in the method of the invention can be found in international patent publications WO 87/3781, WO 93/6089, and WO 94/21606 as well as in European patent application EP 295117, and U.S. Pat. No. 5,232,940. Formulations or compositions for plant growth regulating uses can be made in a similar way, adapting the ingredients, if necessary, to make them more suitable to the plant or soil to which the application is to be made.

The compounds of the formula (I) or their salts can be employed as such or in the form of their preparations (formulations) as combinations with other pesticidally active substances, such as, for example, insecticides, acaricides, nematicides, herbicides, fungicides, safeners, fertilizers and/or further growth regulators, for example as a premix or as tank mixes.

It has been found that, surprisingly, the compounds of formula (I) and most especially compounds 1.1, 1.2, 1.5, 1.7, 1.8, 1.9, 1.10, 1.11, 1.12, 1.13, 2.1, 3.1, 3.2, 3.3, 3.4, 4.1, and 4.5 display a significant role concerning plant growth properties, which can be different due to an application at various crops.

By virtue of the practice of the present invention a wide variety of plant growth responses, including the following (non-ranked listing), may be induced:
a) more developed root system
b) tillering increase
c) increase in plant height
d) bigger leaf blade
e) less dead basal leaves f) stronger tillers
g) greener leaf color
h) less fertilizers needed
i) less seeds needed
j) more productive tillers
k) less third non-productive tillers
l) earlier flowering
m) early grain maturity
n) less plant verse (lodging)
o) longer panicles
p) increased shoot growth
q) improved plant vigour
r) early germination
s) more fruit and better yield It is intended that as used in the instant specification the term "method for plant growth regulation" or "method for plant growth regulation" means the achievement of any of the aforementioned nineteen categories of response or any other modification of plant, seed, fruit or vegetable (whether the fruit or vegetable is nor harvested or harvested) so long as the net result is to increase growth or benefit any property of the plant, seed, fruit or vegetable as distinguished from any pesticidal action (unless the present invention is practised in conjunction with or in the presence of a pesticide, for example a herbicide). The term "fruit" as used in the instant specification is to be understood as meaning anything of economic value that is produced by the plant.

Preferably, at least an increase of 10% of one or more of the respective plant growth response is obtained.

The fused azepinone derivatives of formula (I) may be applied for plant growth regulating purposes to the foliage of plants and/or to the soil in which said plants are growing. Applications to the soil are often in the form of granules which are usually applied in sufficient amount to provide a rate of from about 0.001 kg/ha to about 0.5 kg/ha of active ingredient, preferably between 0.01 and 0.1 kg/ha.

A preferred embodiment of the invention is a method for plant growth regulation comprising applying to the seeds from which said plants grow, prior to said seeds, a non-phytotoxic, effective plant growth regulating amount of a compound having the formula (I). The seed may be treated, especially by coating or embedding or impregnation or soaking or dipping in liquid or paste formulations which are known per se and are subsequently dried. Seed comprising 2 to 1000 gram of a compound of formula (I) per 100 kg, preferably 5 to 800 g per 100 kg, most preferably 5 to 250 g per 100 kg are particularly appropriate for this purpose.

The precise amount of fused azepinone derivatives compound to be used will depend, inter alia, upon the particular plant species being treated. A suitable dose may be determined by the man skilled in the art by routine experimentation. The plant response will depend upon the total amount of compound used, as well as the particular plant species which is being treated. Of course, the amount fused azepinone derivatives should be non-phytotoxic with respect to the plant being treated.

Although the preferred method of application of the compounds used in the process of this invention is directly to the foliage and stems of plants, the compounds can be applied to the soil in which the plants are growing.

The following examples are illustrative of methods of plant growth regulation according to the invention, but should not be understood as limiting the invention as modifications in materials and methods will be apparent to the skilled worker. All measurements of plant growth regulating effects were determined either by using a protoplast screening assay and/or by using a root growth assay and/or by applying the compounds pre-selected the before defined assay system under natural growth conditions in field trials. In all cases, untreated protoplasts, plants or plants parts, or seeds were taken as a control.

B. BIOLOGICAL EXAMPLES

Example 1

Plant Protoplast System

The present invention features a so called high throughput assay for a rapid screening of chemical compounds that modulate cell growth. The assay in general involves: a) plant protoplasts grown in liquid medium, b) a library of chemical compounds, and c) screening the protoplasts to identify the compounds which affect significantly the cell growth and development.

Protoplast Preparation:

Preferably the protoplasts were prepared from cell suspensions derived from maize callus. The protoplasts were obtained by enzymatic digestion of the cell aggregates in the suspension. The cells were digested for 3-6 hours at room temperature in a cellulase-pectolyase mix, Protoplasts were released by gentle shaking, filtered through a 45 µm mesh and collected by centrifugation. After digestion, the protoplasts were washed several times to remove cell debris and enzyme residues and then re-suspended in culture medium. The protoplasts were plated in 50-100 µl aliquots in microtiter wells at a density ranging from 100,000-2,000,000 protoplasts per ml, preferably at a concentration of 800,000 protoplasts/ml.

Screening Assay:

To identify chemical compounds that modulate the cell growth, maize protoplasts were incubated with a library of chemical compounds in 96-well microtiter plates. Following the incubation at 25° C. for 1-14 days, preferably 7-10 days, the protein content was measured by Coomassie dye based colorimetric assays. The growth of the cells treated with the chemical compounds involved in the test was detected by comparison with untreated protoplasts.

Treatment with a section of compounds derived from formula (I) show an increase of more than 50% over untreated control.

Example 2

Root Growth Assay

Plant roots are a highly proliferative tissue that allows an easy accessible, cheap and short term screening method for plant growth regulators. The results obtained can easily be transferred to the overall effects on a plant of plant growth regulators identified by such a system. By using this root assay one is enabled to determine the effect of a seed treatment to root growth and/or germination and/or changes in habitat of germinated plants in order to identify the possible use as a yield enhancer. Two seeds of wheat (*Triticum aestivum*, variety "TRISO") or 1 seed of maize (*Zea mays*, variety "LORENZO") per hole in a plastic tray which contains an architecture of 8×13 holes were placed on compost soil covered with sand. These seeds were treated with 100 µl/hole, which creates an application volume of approx. 1200 l/ha, of a compound solution at active ingredient rates equivalent to 100, 10 and 1 g a.i./ha of each compound using an robotic application system (Lizzy Spray Robotics). Six replicates in a row of each compound and concentration were done. The outer rim of the above defined plastic tray was untreated to avoid false negative effects and the middle row (No. 7) was used as untreated control. The treated seeds were allowed to dry for approx. 4 hours and subsequently covered with sand and watered. The trays were stored in climate chambers with 14 hours lighting at a temperature of 24° C. (±2) at daytime and 16° C. (±2) at night and relative humidity (rH) of 60% and daily watered. Assessments were done 16 (±2) days post treatment by counting the germinated plants and assessing the phytotoxicity symptoms and percentage. In addition, the roots were washed out and the shoots were cut directly above the seed and the wet roots were placed on dry paper towels for approximately 30 minutes and weighted afterwards. This procedure provides a similar grade of moisture to the roots so that a comparison of the weights is possible.

Table 5 shows the results of some of the compounds (Cpd) claimed to be effective in plant growth regulation concerning maize. The effects observed concerning Root Growth given in column 2 (Root Growth of "100" is set as the standard) are directed to concentrations that are equivalent to 100, 10, 1 g a.i./ha, each.

TABLE 5

| | Maize (concentration g a.i./ha) | | |
|---|---|---|---|
| Cpd | 100 | 10 | 1 |
| 1.7 | 136 | 138 | 133 |
| 1.8 | 115 | 78 | 112 |
| 1.12 | 161 | 109 | 117 |
| 3.1 | 86 | 150 | 86 |
| 3.2 | 123 | 89 | 96 |
| 3.4 | 144 | 121 | 85 |
| 4.1 | 136 | 102 | 131 |

Table 6 shows the results of some of the compounds (Cpd) claimed to be effective in plant growth regulation concerning wheat. The effects observed concerning Root Growth given in column 2 (Root Growth of "100" is set as the standard) are directed to concentrations that are equivalent to 100, 10, 1 g a.i./ha, each.

TABLE 6

| | Wheat (concentration g a.i./ha) | | |
|---|---|---|---|
| Cpd | 100 | 10 | 1 |
| 1.5 | 93 | 121 | 78 |
| 3.1 | 135 | 125 | 98 |
| 3.2 | 98 | 131 | 133 |
| 3.4 | 195 | 126 | 125 |
| 4.5 | 79 | 106 | 149 |

Example 3

Glasshouse Trial

Seed treatments containing the chemicals were applied to wheat seed as a seed treatment at rates of 0, 1, 10 and 100 mg of compound (Cpd) per kg of seed using a randomized complete block design with 3 replications.

The seed treatments were prepared by dissolving the chemicals in DMSO at a concentration of 1 mg/ml, making the appropriate dilutions, and mixing chemical solutions with an equal volume of the seed coating solution Raxil-MD (Gustafson). The seed treatments containing the chemicals were applied to seed by combining 25 g of wheat seed (Dirkwin var.) with 140 µl of the seed treatment in a sealed bag and thoroughly mixing them until the seed are evenly coated.

The treated seeds were planted in trays containing 25 pots (7.3 cm×7.3 cm×22.9 cm tall) filled with Pro-Mix HP mixed with Osmocoat fertilizer (680 g of Osmocote (15-9-12) per 32 kg Pro Mix 15-9-12) allowed to germinate and thinned to a single plant per pot. Plants were grown in the Glasshouse maintained at 20° C. during the day and 16° C. at night. Light was supplemented with 75 µEi of light from high pressure sodium bulbs to provide a 16 h day and 8 h night. When the plants matured, seed was harvested and cleaned from all the plants in a tray. The mass of the seeds was measured and recorded in Gram seed yield/Tray. Table 7 shows the results obtained by using compound 1.12 at various application rates.

TABLE 7

| Treatment (mg Cpd 1.12/kg seed) | Seed yield g/Tray |
|---|---|
| 0 | 26.8 |
| 1 | 35.4 |
| 10 | 41.9 |
| 100 | 43.7 |

The invention claimed is:

1. A method of regulating plant growth, comprising applying an effective plant growth regulating amount of a compound of formula (I) or an agriculturally acceptable salt thereof to a plant, to the seed from which the plant grows or to the locus where the plant grows, said compound of formula (I) having the structure:

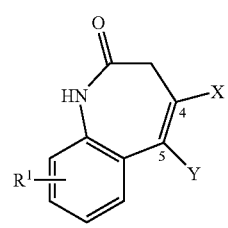

(I)

wherein:

X is $CO_2R^2$ or H;

Y is OH, $NHNR^3R^4$, $NHNHC(=Z)NR^5R^6$ or $NHNHC(=Z)CR^7R^8R^9$; or

X and Y together with the two carbon atoms to which they are attached form a ring of formula (A):

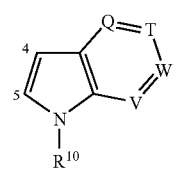

(A)

wherein the carbon atoms marked 4 and 5 respectively correspond to the carbon atoms marked 4 and 5 in formula (I);

Q, T, W and V are each independently $CR^{11}$ or a N atom, providing that only one of Q, T, W and V is a N atom;

Z is O or S;

$R^1$ and $R^{11}$ are each independently selected from the group consisting of H, halogen, hydroxy, amino, nitro, formyl, carboxy, cyano, thiocyanato, aminocarbonyl, $(C_1-C_6)$ alkoxy, $(C_1-C_6)$haloalkoxy, $(C_1-C_6)$alkyl-$S(O)_n$, $(C_1-C_6)$haloalkyl-$S(O)_n$, $(C_1-C_6)$alkylamino, di[$(C_1-C_6)$ alkyl]amino, $(C_1-C_6)$alkylcarbonyl, $(C_1-C_6)$ alkoxycarbonyl, $(C_1-C_6)$alkylaminocarbonyl, di[$(C_1-C_6)$alkyl]aminocarbonyl, N—$(C_1-C_6)$alkanoylamino, N—$(C_1-C_6)$alkanoyl-N—$(C_1-C_6)$alkylamino, sulfamoyl, N—$(C_1-C_6)$alkylsulfamoyl, N,N-di[$(C_1-C_6)$ alkyl]sulfamoyl, $(C_3-C_9)$cycloalkyl, $(C_1-C_6)$alkyl, $(C_2-C_6)$alkenyl and $(C_2-C_6)$alkynyl, where each of the $(C_1-C_6)$alkyl, $(C_2-C_6)$alkenyl or $(C_2-C_6)$alkynyl radicals is unsubstituted or substituted by one or more radicals selected from the group consisting of halogen, hydroxy, amino, nitro, carboxy, cyano, $(C_1-C_4)$alkoxy, $(C_1-C_4)$ haloalkoxy, $(C_1-C_4)$alkyl-$S(O)_n$, $(C_1-C_4)$haloalkyl-$S(O)_n$, $(C_1-C_4)$alkylamino, di[$(C_1-C_4)$alkyl]amino, $(C_3-C_9)$cycloalkyl, $(C_1-C_4)$alkylcarbonyl, $(C_1-C_4)$ alkoxycarbonyl, phenyl, phenoxy, phenylthio, heterocyclyl, heteroaryloxy and heteroarylthio, where each of the phenyl, phenoxy, phenylthio, heterocyclyl, heteroaryloxy or heteroarylthio radicals is unsubstituted or has one or more substituents selected from the group consisting of halogen, nitro, formyl, cyano, $(C_1-C_4)$ alkyl, $(C_1-C_4)$alkoxy, $(C_1-C_4)$alkyl-$S(O)_n$, $(C_1-C_4)$haloalkyl-$S(O)_n$, $(C_1-C_4)$haloalkyl, $(C_1-C_4)$haloalkoxy, $(C_1-C_4)$alkylcarbonyl and $(C_1-C_4)$alkoxycarbonyl;

or are each independently selected from the group consisting of phenyl, phenoxy, phenylthio, phenylcarbonyl, heteroaryl, heteroaryloxy and heteroarylthio, unsubstituted or substituted by one or more radicals selected from the group consisting of halogen, hydroxy, amino, nitro, carboxy, formyl, cyano, $(C_1-C_4)$alkyl, $(C_1-C_4)$haloalkyl, $(C_1-C_4)$alkoxy, $(C_1-C_4)$haloalkoxy, $(C_1-C_4)$ alkyl-$S(O)_n$, $(C_1-C_4)$haloalkyl-$S(O)_n$, $(C_1-C_4)$alkylamino, di[$(C_1-C_4)$alkyl]amino, $(C_1-C_4)$alkylcarbonyl, $(C_1-C_4)$alkoxycarbonyl and in the case of heteroaryl also oxo, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated; and said heterocyclyl is a heterocyclic radical having 3 to 7 ring atoms and 1 to 3 hetero atoms selected from the group consisting of N, O and S;

$R^2$ is $(C_1-C_6)$alkyl, $(C_3-C_9)$cycloalkyl, $(C_1-C_6)$alkyl, $(C_2-C_6)$alkenyl, $(C_2-C_6)$alkynyl, or $(C_1-C_4)$alkoxy-$(C_1-C_4)$ alkyl;

$R^3$ is $(C_1-C_6)$alkyl, $(C_2-C_6)$alkenyl, $(C_2-C_6)$alkynyl, phenyl-$(CH_2)_m$ or heteroaryl, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated which is unsubstituted or substituted by one or more radicals selected from the group consisting of halogen, hydroxy, amino, nitro, carboxy, formyl, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-$S(O)_n$, $(C_1-C_4)$haloalkyl-$S(O)_n$, $(C_1-C_4)$alkylamino, di[$(C_1-C_4)$alkyl]amino, $(C_1-C_4)$alkylcarbonyl, $(C_1-C_4)$ alkoxycarbonyl and oxo;

$R^4$, $R^6$, $R^8$, $R^9$ and $R^{10}$ are each independently H or $(C_1-C_6)$ alkyl;

$R^5$ is H or $R^3$;

$R^7$ is as defined for $R^3$ wherein m is zero;

m is 0 or 1; and n is 0, 1 or 2.

2. The method of claim 1, in which

Y is OH; or

X and Y together with the two carbon atoms to which they are attached form a ring of formula (A).

3. The method of claim 1, in which

X is $CO_2R^2$ or H; and Y is OH; or

X and Y together with the two carbon atoms to which they are attached form a ring of formula (A), wherein Q, T, W and V are each $CR^{11}$, $R^{11}$ is as defined in claim 1, and $R^{10}$ is H.

4. The method of claim 1, in which $R^1$ and $R^{11}$ are each independently selected from the group consisting of H, halogen, hydroxy, amino, nitro, formyl, carboxy, cyano, thiocyanato, aminocarbonyl, $(C_1-C_4)$ alkoxy, $(C_1-C_4)$haloalkoxy, $(C_1-C_4)$alkyl-$S(O)_n$, $(C_1-C_4)$haloalkyl-$S(O)_n$, $(C_1-C_4)$alkylamino, di[$(C_1-C_4)$] alkylamino, $(C_1-C_4)$alkylcarbonyl, $(C_1-C_4)$ alkoxycarbonyl, $(C_1-C_4)$alkylaminocarbonyl, di[$(C_1-C_4)$alkyl]aminocarbonyl, N—$(C_1-C_4)$alkanoylamino, N—$(C_1-C_4)$alkanoyl-N—$(C_1-C_4)$alkylamino, sulfamoyl, N—$(C_1-C_4)$alkylsulfamoyl, N,N-di[$(C_1-C_4)$ alkyl]sulfamoyl, $(C_3-C_6)$cycloalkyl, $(C_1-C_4)$alkyl, $(C_2-C_4)$alkenyl and $(C_2-C_4)$alkynyl, where each of the $(C_1-C_4)$alkyl, $(C_2-C_4)$alkenyl or $(C_2-C_4)$alkynyl radicals is unsubstituted or substituted by one or more radicals selected from the group consisting of halogen, hydroxy, amino, nitro, carboxy, cyano, $(C_1-C_4)$alkoxy, $(C_1-C_4)$ haloalkoxy, $(C_1-C_4)$alkyl-$S(O)_n$, $(C_1-C_4)$haloalkyl-$S(O)_n$, $(C_1-C_4)$alkylamino, di[$(C_1-C_4)$alkyl]amino, $(C_3-C_6)$cycloalkyl, $(C_1-C_4)$alkylcarbonyl, $(C_1-C_4)$ alkoxycarbonyl, phenyl, phenoxy, phenylthio, heterocyclyl, heteroaryloxy and heteroarylthio, where each of the phenyl, phenoxy, phenylthio, heterocyclyl, heteroaryloxy or heteroarylthio radicals is unsubstituted or has one or more substituents selected from the group consisting of halogen, nitro, cyano, $(C_1-C_4)$alkyl, $(C_1-C_4)$alkoxy, $(C_1-C_4)$alkyl-$S(O)_n$, $(C_1-C_4)$haloalkyl-$S(O)_n$, $(C_1-C_4)$haloalkyl, $(C_1-C_4)$haloalkoxy, $(C_1-C_4)$ alkylcarbonyl and $(C_1-C_4)$alkoxycarbonyl;

or are each independently selected from the group consisting of phenyl, phenoxy, phenylthio, phenylcarbonyl, heteroaryl, heteroaryloxy and heteroarylthio, unsubstituted or substituted by one or more radicals selected from the group consisting of halogen, hydroxy, amino, nitro, carboxy, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-$S(O)_n$, $(C_1-C_4)$haloalkyl-$S(O)_n$, $(C_1-C_4)$alkylamino, di[$(C_1-C_4)$alkyl]amino, $(C_1-C_4)$alkylcarbonyl, $(C_1-C_4)$ alkoxycarbonyl and in the case of heteroaryl also oxo, where said heteroaryl is a mono-, bi- or tricyclic heteroaromatic ring system in which at least one ring contains one or more hetero atoms selected from the group consisting of N, O and S, and which contains a total of 5 to ring atoms wherein at least one ring is fully unsaturated; and said heterocyclyl is a heterocyclic radical having 3 to 7 ring atoms and 1 to 3 hetero atoms selected from the group consisting of N, O and S.

5. The method of claim 1, in which $R^1$ and $R^{11}$ are each independently selected from the group consisting of H, halogen, hydroxy, amino, nitro, formyl, carboxy, cyano, thiocyanato, aminocarbonyl, $(C_1-C_4)$ alkoxy, (C₁-C₄)haloalkoxy, (C₁-C₄)alkyl-S(O)ₙ, (C₁-C₄)haloalkyl-S(O)ₙ, (C₁-C₄)alkylamino, di[(C₁-C₄)alkyl]amino, (C₁-C₄)alkylcarbonyl, (C₁-C₄)alkoxycarbonyl, (C₁-C₄)alkylaminocarbonyl, di[(C₁-C₄)alkyl]aminocarbonyl, N—(C₁-C₄)alkanoylamino, N—(C₁-C₄)alkanoyl-N—(C₁-C₄)alkylamino, sulfamoyl, N—(C₁-C₄)alkylsulfamoyl, N,N-di[(C₁-C₄)alkyl]sulfamoyl, (C₃-C₆)cycloalkyl, (C₁-C₄)alkyl, (C₂-C₄)alkenyl and (C₂-C₄)alkynyl, where each of the (C₁-C₄)alkyl, (C₂-C₄)alkenyl or (C₂-C₄)alkynyl radicals is unsubstituted or substituted by one or more radicals selected from the group consisting of halogen, hydroxy, amino, cyano, (C₁-C₄)alkoxy, (C₁-C₄)haloalkoxy, (C₁-C₄)alkyl-amino, di[(C₁-C₄)alkyl]amino, (C₃-C₆)cycloalkyl, (C₁-C₄)alkoxycarbonyl and phenyl, where the phenyl radical is unsubstituted or has one or more substituents selected from the group consisting of halogen, nitro, cyano, (C₁-C₄)alkyl, (C₁-C₄)alkoxy, (C₁-C₄)alkyl-S(O)ₙ, (C₁-C₄)haloalkyl-S(O)ₙ, (C₁-C₄)haloalkyl, (C₁-C₄)haloalkoxy, (C₁-C₄)alkylcarbonyl and (C₁-C₄)alkoxycarbonyl;

or are each independently selected from the group consisting of phenyl, phenoxy and heteroaryl, unsubstituted or substituted by one or more radicals selected from the group consisting of halogen, hydroxy, amino, nitro, carboxy, cyano, (C₁-C₄)alkyl, (C₁-C₄)haloalkyl, (C₁-C₄)alkoxy, (C₁-C₄)haloalkoxy, (C₁-C₄)alkyl-S(O)ₙ, (C₁-C₄)haloalkyl-S(O)ₙ, (C₁-C₄)alkylamino, di[(C₁-C₄)alkyl]amino, (C₁-C₄)alkylcarbonyl, (C₁-C₄)alkoxycarbonyl and in the case of heteroaryl also oxo, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated; and said heterocyclyl is a heterocyclic radical having 3 to 7 ring atoms and 1 to 3 hetero atoms selected from the group consisting of N, O and S.

6. The method of claim 1, in which

R¹ and R¹¹ are each independently selected from the group consisting of H, halogen, OH, NO₂, CN, CO₂H, (C₁-C₄)alkyl, (C₁-C₄)haloalkyl, (C₁-C₄)alkoxy-(C₁-C₄)alkyl, (C₁-C₄)alkoxy, (C₁-C₄)alkylcarbonyl and (C₁-C₄)alkoxycarbonyl.

7. The method of claim 1, in which

X is CO₂R² or H; and Y is OH; or

X and Y together with the two carbon atoms to which they are attached form a ring of formula (A) above, wherein Q, T, W and V are each CR¹¹;

R¹ and R¹¹ are each independently selected from the group consisting of H, halogen, hydroxy, amino, nitro, formyl, carboxy, cyano, thiocyanato, aminocarbonyl, (C₁-C₄)alkoxy, (C₁-C₄)haloalkoxy, (C₁-C₄)alkyl-S(O)ₙ, (C₁-C₄)haloalkyl-S(O)ₙ), (C₁-C₄)alkylamino, di[(C₁-C₄)alkyl]amino, (C₁-C₄)alkylcarbonyl, (C₁-C₄)alkoxycarbonyl, (C₁-C₄)alkylaminocarbonyl, di[(C₁-C₄)alkyl]aminocarbonyl, N—(C₁-C₄)alkanoylamino, N—(C₁-C₄)alkanoyl-N—(C₁-C₄)alkylamino, sulfamoyl, N—(C₁-C₄)alkylsulfamoyl, N,N-di[(C₁-C₄)alkyl]sulfamoyl, (C₃-C₆)cycloalkyl, (C₁-C₄)alkyl, (C₂-C₄)alkenyl and (C₂-C₄)alkynyl, where each of the (C₁-C₄)alkyl, (C₂-C₄)alkenyl or (C₂-C₄)alkynyl radicals is unsubstituted or substituted by one or more radicals selected from the group consisting of halogen, hydroxy, amino, nitro, carboxy, cyano, (C₁-C₄)alkoxy, (C₁-C₄)haloalkoxy, (C₁-C₄)alkyl-S(O)ₙ, (C₁-C₄)haloalkyl-S(O)ₙ, (C₁-C₄)alkylamino, di[(C₁-C₄)alkyl]amino, (C₃-C₆)cycloalkyl, (C₁-C₄)alkylcarbonyl, (C₁-C₄)alkoxycarbonyl, phenyl, phenoxy, phenylthio, heterocyclyl, heteroaryloxy and heteroarylthio, where each of the phenyl, phenoxy, phenylthio, heterocyclyl, heteroaryloxy or heteroarylthio radicals is unsubstituted or has one or more substituents selected from the group consisting of halogen, nitro, cyano, (C₁-C₄)alkyl, (C₁-C₄)alkoxy, (C₁-C₄)alkyl-S(O)ₙ, (C₁-C₄)haloalkyl-S(O)ₙ, (C₁-C₄)haloalkyl, (C₁-C₄)haloalkoxy, (C₁-C₄)alkylcarbonyl and (C₁-C₄)alkoxycarbonyl;

or are each independently selected from the group consisting of phenyl, phenoxy, phenylthio, phenylcarbonyl, heteroaryl, heteroaryloxy and heteroarylthio, unsubstituted or substituted by one or more radicals selected from the group consisting of halogen, hydroxy, amino, nitro, carboxy, cyano, (C₁-C₄)alkyl, (C₁-C₄)haloalkyl, (C₁-C₄)alkoxy, (C₁-C₄)haloalkoxy, (C₁-C₄)alkyl-S(O)ₙ, (C₁-C₄)haloalkyl-S(O)ₙ, (C₁-C₄)alkylamino, di[(C₁-C₄)alkyl]amino, (C₁-C₄)alkylcarbonyl, (C₁-C₄)alkoxycarbonyl and in the case of heteroaryl also oxo, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated; and said heterocyclyl is a heterocyclic radical having 3 to 7 ring atoms and 1 to 3 hetero atoms selected from the group consisting of N, O and S; and R¹⁰ is H.

8. A method of regulating plant growth, comprising applying an effective amount of a composition comprising one or more compounds of formula (I) or agriculturally acceptable salts thereof in an amount effective for plant growth regulation, and one or more carriers or surfactants useful for plant protection formulations to a plant, to the seed from which the plant grows or to the locus where the plant grows, wherein the plant is a monocotyledoneous or dicotyledoneous crop plant, said compound of formula (I) having the structure:

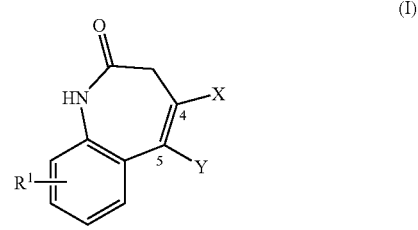

(I)

wherein:

X is CO₂R² or H;

Y is OH, NHNR³R⁴, NHNHC(=Z)NR⁵R⁶ or NHNHC(=Z)CR⁷R⁸R⁹; or

X and Y together with the two carbon atoms to which they are attached form a ring of formula (A):

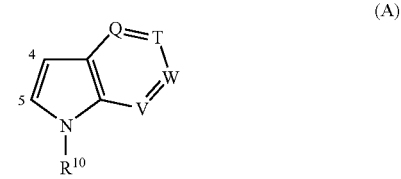

(A)

wherein the carbon atoms marked 4 and 5 respectively correspond to the carbon atoms marked 4 and 5 in formula (I);

Q, T, W and V are each independently $CR^{11}$ or a N atom, providing that only one of Q, T, W and V is a N atom;

Z is O or S;

$R^1$ and $R^{11}$ are each independently selected from the group consisting of H, halogen, hydroxy, amino, nitro, formyl, carboxy, cyano, thiocyanato, aminocarbonyl, $(C_1-C_6)$ alkoxy, $(C_1-C_6)$haloalkoxy, $(C_1-C_6$alkyl-$S(O)_n$, $(C_1-C_6)$ haloalkyl-$S(O)_n$, $(C_1-C_6)$alkylamino, di[$(C_1-C_6)$alkyl] amino, $(C_1-C_6)$alkylcarbonyl, $(C_1-C_6)$alkoxycarbonyl, $(C_1-C_6)$alkylaminocarbonyl, di[$(C_1-C_6)$alkyl]aminocarbonyl, N—$(C_1-C_6)$alkanoylamino, N—$(C_1-C_6)$alkanoyl-N—$(C_1-C_6)$alkylamino, sulfamoyl, N—$(C_1-C_6)$ alkylsulfamoyl, N,N-di[$(C_1-C_6)$alkyl]sulfamoyl, $(C_3-C_9)$cycloalkyl, $(C_1-C_6)$alkyl, $(C_2-C_6)$alkenyl and $(C_2-C_6)$alkynyl, where each of the $(C_1-C_6)$alkyl, $(C_2-C_6)$ alkenyl or $(C_2-C_6)$alkynyl is unsubstituted or substituted by one or more radicals selected from the group consisting of halogen, hydroxy, amino, nitro, carboxy, cyano, $(C_1-C_4)$alkoxy, $(C_1-C_4)$haloalkoxy $(C_1-C_4)$alkyl-$S(O)_n$, $C_1-C_4)$haloalkyl-$S(O)_n$, $(C_1-C_4)$alkylamino, di[$(C_1-C_4)$ alkyl]amino, $(C_3-C_9)$cycloalkyl, $(C_1-C_4)$alkylcarbonyl, $(C_1-C_4)$alkoxycarbonyl, phenyl, phenoxy, phenylthio, heterocyclyl, heteroaryloxy and heteroarylthio, where each of the phenyl, phenoxy, phenylthio, heterocyclyl, heteroaryloxy or heteroarylthio radicals is unsubstituted or has one or more substituents selected from the group consisting of halogen, nitro, formyl, cyano, $(C_1-C_4)$ alkyl, $(C_1-C_4)$alkoxy, $(C_1-C_4)$alkyl-$S(O)_n$, $(C_1-C_4)$haloalkyl-$S(O)_n$, $(C_1-C_4)$haloalkyl, $(C_1-C_4)$haloalkoxy, $(C_1-C_4)$alkylcarbonyl and $(C_1-C_4)$alkoxycarbonyl;

or are each independently selected from the group consisting of phenyl, phenoxy, phenylthio, phenylcarbonyl, heteroaryl, heteroaryloxy and heteroarylthio, unsubstituted or substituted by one or more radicals selected from the group consisting of halogen, hydroxy, amino, nitro, carboxy, formyl, cyano, $(C_1-C_4)$alkyl, $(C_1-C_4)$haloalkyl, $(C_1-C_4)$alkoxy, $(C_1-C_4)$haloalkoxy, $(C_1-C_4)$ alkyl-$S(O)_n$, $(C_1-C_4)$haloalkyl-$S(O)_n$, $(C_1-C_4)$alkylamino, di[$(C_1-C_4)$alkyl]amino, $(C_1-C_4)$alkylcarbonyl, $(C_1-C_4)$alkoxycarbonyl and in the case of heteroaryl also oxo, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated; and said heterocyclyl is a heterocyclic radical having 3 to 7 ring atoms and 1 to 3 hetero atoms selected from the group consisting of N, O and S;

$R^2$ is $(C_1-C_6)$alkyl, $(C_3-C_9)$cycloalkyl, $(C_1-C_6)$alkyl, $(C_2-C_6)$alkenyl, $(C_2-C_6)$alkynyl, or $(C_1-C_4)$alkoxy-$(C_1-C_4)$ alkyl;

$R^3$ is $(C_1-C_6)$alkyl, $(C_2-C_6)$alkenyl, $(C_2-C_6)$alkynyl, phenyl-$(CH_2)_m$ or heteroaryl, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated which is unsubstituted or substituted by one or more radicals selected from the group consisting of halogen, hydroxy, amino, nitro, carboxy, formyl, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-S $(O)_n$, $C_1-C_4)$haloalkyl-$S(O)_n$, $(C_1-C_4)$alkylamino, di[$(C_1-C_4)$alkyl]amino, $(C_1-C_4)$alkylcarbonyl, $(C_1-C_4)$ alkoxycarbonyl and oxo;

$R^4$, $R^6$, $R^8$, $R^9$ and $R^{10}$ are each independently H or $(C_1-C_6$ alkyl;

$R^5$ is H or $R^3$;

$R^7$ is as defined for $R^3$ wherein m is zero;

m is 0 or 1; and n is 0, 1 or 2.

9. The method of claim 8 wherein in the composition further comprises an active compound selected from the group consisting of an acaricide, a fungicide, an herbicide, an insecticide, a nematicide and a plant growth regulating substance not identical to the compound of formula (I) as defined in claim 8.

10. The method as claimed in claim 8, wherein the plant is selected from the group consisting of wheat, barley, rye, triticale, rice, maize, sugar beet, cotton, and soybean.

11. A method of regulating growth of crop plants, which comprises applying an effective amount of one or more compounds of formula (I) or agriculturally acceptable salts thereof to said plants, to the seeds from which they grow or to the locus in which they grow, wherein said effective amount is a non-phytotoxic, effective plant growth regulating amount and said one or more compounds of formula (I) has the structure:

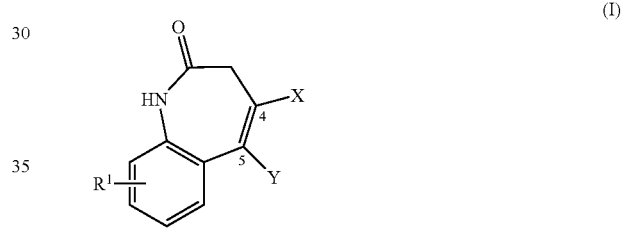

(I)

wherein:

X is $CO_2R^2$ or H;

Y is OH, $NHNR^3R^4$, NHNHC(=Z)$NR^5R^6$ or NHNHC (=Z)$CR^7R^8R^9$; or

X and Y together with the two carbon atoms to which they are attached form a ring of formula (A):

(A)

wherein the carbon atoms marked 4 and 5 respectively correspond to the carbon atoms marked 4 and 5 in formula (I);

Q, T, W and V are each independently $CR^{11}$ or an N atom, providing that only one of Q, T, W and V is a N atom;

Z is O or S;

$R^1$ and $R^{11}$ are each independently selected from the group consisting of H, halogen, hydroxy, amino, nitro, formyl, carboxy, cyano, thiocyanato, aminocarbonyl, $(C_1-C_6)$ alkoxy, $(C_1-C_6)$haloalkoxy, $(C_1-C_6)$alkyl-$S(O)_n$, $(C_1-C_6)$haloalkyl-$S(O)_n$, $(C_1-C_6)$alkylamino, di[$(C_1-C_6)$ alkyl]amino, $(C_1-C_6)$alkylcarbonyl, $(C_1-C_6)$ alkoxycarbonyl, $(C_1-C_6)$alkylaminocarbonyl, di[$(C_1-C_6)$alkyl]aminocarbonyl, N—$(C_1-C_6)$alkanoylamino, N—$(C_1-C_6)$alkanoyl-N—$(C_1-C_6)$alkylamino, sulfamoyl, N—$(C_1-C_6)$alkylsulfamoyl, N,N-di[$(C_1-C_6)$alkyl]sulfamoyl, $(C_3-C_9)$cycloalkyl, $(C_1-C_6)$alkyl, $(C_2-C_6)$alkenyl and $(C_2-C_6)$alkynyl, where each of the $(C_1-C_6)$alkyl, $(C_2-C_6)$alkenyl or $(C_2-C_6)$alkynyl radicals is unsubstituted or substituted by one or more radicals selected from the group consisting of halogen, hydroxy, amino, nitro, carboxy, cyano, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_3-C_9)$cycloalkyl, $(C_1-C_4)$alkylcarbonyl, $(C_1-C_4)$alkoxycarbonyl, phenyl, phenoxy, phenylthio, heterocyclyl, heteroaryloxy and heteroarylthio, where each of the phenyl, phenoxy, phenylthio, heterocyclyl, heteroaryloxy or heteroarylthio radicals is unsubstituted or has one or more substituents selected from the group consisting of halogen, nitro, formyl, cyano, $(C_1-C_4)$alkyl, $(C_1-C_4)$alkoxy, $(C_1-C_4)$alkyl-S(O)$_n$, $(C_1-C_4)$haloalkyl-S(O)$_n$, $(C_1-C_4)$haloalkyl, $(C_1-C_4)$haloalkoxy, $(C_1-C_4)$alkylcarbonyl and $(C_1-C_4)$alkoxycarbonyl;

or are each independently selected from the group consisting of phenyl, phenoxy, phenylthio, phenylcarbonyl, heteroaryl, heteroaryloxy and heteroarylthio, unsubstituted or substituted by one or more radicals selected from the group consisting of halogen, hydroxy, amino, nitro, carboxy, formyl, cyano, $(C_1-C_4)$alkyl, $(C_1-C_4)$haloalkyl, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_1-C_4)$alkylcarbonyl, $(C_1-C_4)$alkoxycarbonyl and in the case of heteroaryl also oxo, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated; and said heterocyclyl is a heterocyclic radical having 3 to 7 ring atoms and 1 to 3 hetero atoms selected from the group consisting of N, O and S;

$R^2$ is $(C_1-C_6)$alkyl, $(C_3-C_9)$cycloalkyl, $(C_1-C_6)$alkyl, $(C_2-C_6)$alkenyl, $(C_2-C_6)$alkynyl, or $(C_1-C_4)$alkoxy-$(C_1-C_4)$alkyl;

$R^3$ is $(C_1-C_6)$alkyl, $(C_2-C_6)$alkenyl, $(C_2-C_6)$alkynyl, phenyl-$(CH_2)_m$ or heteroaryl, where said heteroaryl is a mono-, bi- or tricyclic heteroaromatic ring system in which at least 1 ring contains one or more hetero atoms selected from the group consisting of N, O and S, and which contains a total of 5 to 14 ring atoms wherein at least one ring is fully unsaturated which is unsubstituted or substituted by one or more radicals selected from the group consisting of halogen, hydroxy, amino, nitro, carboxy, formyl, cyan, $(C_1-C_4)$alkyl, $(C_1-C_4)$haloalkyl, $(C_1-C_4)$alkoxy, $(C_1-C_4)$haloalkoxy, $(C_1-C_4)$alkyl-S(O)$_n$, $(C_1-C_4)$haloalkyl-S(O)$_n$, $(C_1-C_4)$alkylamino, di[$(C_1-C_4)$alkyl]amino, $(C_1-C_4)$alkylcarbonyl, $(C_1-C_4)$alkoxycarbonyl and oxo;

$R^4$, $R^6$, $R^8$, $R^9$ and $R^{10}$ are each independently H or $(C_1-C_6)$alkyl;

$R^5$ is H or $R^3$;

$R^7$ is as defined for $R^3$ wherein m is zero;

m is 0 or 1; and n is 0, 1 or 2.

12. The method as claimed in claim 11, wherein said method results in an increase of at least 10% of the yield of the plant to which said one or more compounds of formula (I) is applied.

\* \* \* \* \*